United States Patent [19]
Panicali et al.

[11] Patent Number: 5,242,829
[45] Date of Patent: Sep. 7, 1993

[54] RECOMBINANT PSEUDORABIES VIRUS

[75] Inventors: Dennis L. Panicali, Acton; Gail P. Mazzara, Winchester; Linda R. Gritz, Somerville, all of Mass.

[73] Assignee: Therion Biologics Corporation, Cambridge, Mass.

[21] Appl. No.: 492,417

[22] Filed: Mar. 6, 1990

Related U.S. Application Data

[63] Continuation of Ser. No. 910,501, Sep. 23, 1986, abandoned.

[51] Int. Cl.$^5$ ............................................. C12N 15/86
[52] U.S. Cl. ................................ 435/320.1; 435/69.1; 435/172.3; 435/69.3; 424/89
[58] Field of Search ................ 435/69.3, 320.1, 172.3; 424/89

[56] References Cited

U.S. PATENT DOCUMENTS 4,603,112  7/1986  Paoletti et al. .................... 435/235.1

FOREIGN PATENT DOCUMENTS 110385      6/1984   European Pat. Off.
0162738    11/1985   European Pat. Off.
WO87/02058  4/1987   PCT Int'l Appl.

OTHER PUBLICATIONS

Mackett et al, Journal of Virology 49:857–864 (1984) General Method for Production and Selection of Infectious Vaccinia Virus Recombinants Expressing Foreign Genes.
Smith et al, PNAS 80: 7155–7159 (1983) Construction of infectious vaccinia virus recombinant that expresses influenza HA gene . . . .
Boyle et al, Gene 35(2): 169–177 (1985) Multiple cloning site plasmids for the rapid construction of recombinant pox viruses.
Chakrabarti et al, Mol. Cell Biol. 5: 3403–3409 (1985).
Perkus et al, Science 229: 981–984 (1985) Recombinant Vaccinia Virus: Immunization Against Multiple Pathogens.
Hampl et al, J. Virol. 52: 583–590 Characterization of Envelope Proteins of PRV (1984).
Wathen et al, J. Virol. 51: 57–62 (1984) Isolation, Characterization, & Physical Mapping of PRV mutant . . . gp50.
Panicali, D. et al., Gene 47:193–199 (1986).
Li et al., J. Virol. 62:776–782 (1988).
Turner et al., Virology 173:509–521 (1989).
Fuerst et al., Mol. Cell. Biol. 7:2538–2544 (1987).
Gillespie et al., J. Clin. Microbiol. 23:283–288 (1986).
Martin et al., J. Virol. 61:726–734 (1987).
Martin et al., J. Immunol. 138:3431–3437 (1987).
Morgan et al., Abstract from Herpes Virus Workshop (1987).
Petrovskis, E. A. et al., J. Virol. 59(2):216–223 (1986).
Robbins, A. K. et al. "Identification of a PRV Glycoprotein Gene Using a Heterologous DNA Probe from Herpes Simplex Virus", Tenth International Herpes Virus Workshop, Ann Arbor, Mich., Aug. 11–16, 1985, p. 130.
Robbins, A. K. et al., J. Virol. 58(2) 339 (1986).
Wittek et al. (1984) J. Virol. 49, 371.
Bertholet et al., (1985) Proc. Nat'l. Acad. Sci. USA 82, 2096.
Venkatesan et al. (1981) Cell 25, 805.

Primary Examiner—Richard A. Schwartz
Assistant Examiner—David Guzo
Attorney, Agent, or Firm—Sewall P. Bronstein; Ronald I. Eisenstein; David S. Resnick

[57] ABSTRACT

Monovalent and multivalent recombinant pox viruses which express immunogenic proteins of pseudorabies viruses are provided for use as live vaccines against pseudorabies virus. DNA vectors for recombination with pox virus to introduce one or more genes into a pox viral genome are also provided.

3 Claims, 20 Drawing Sheets

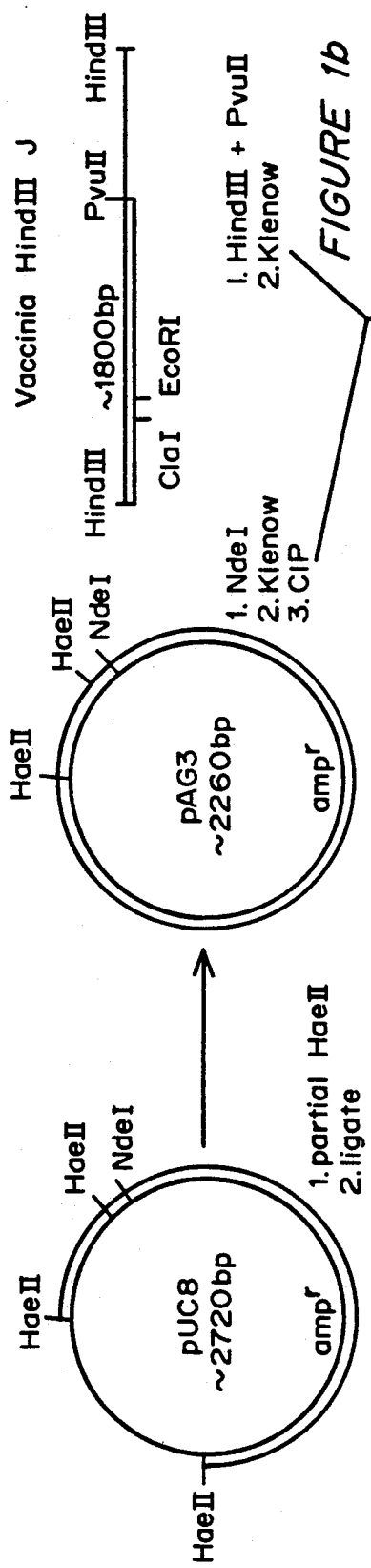
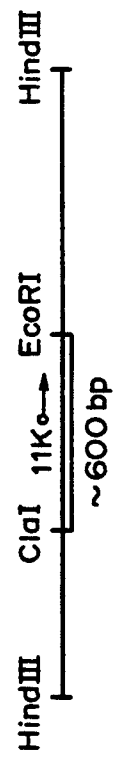
FIGURE 1a
FIGURE 1b
FIGURE 1c
Figure 1c continued on Figure 1d Sequence of 11K and 11KΔ5-pEMBL19 junction 11K   CTATGCTATAA<u>ATG</u>AATT---

11KΔ5 CTATGCTATCGACTCTAG-----pEMBL19

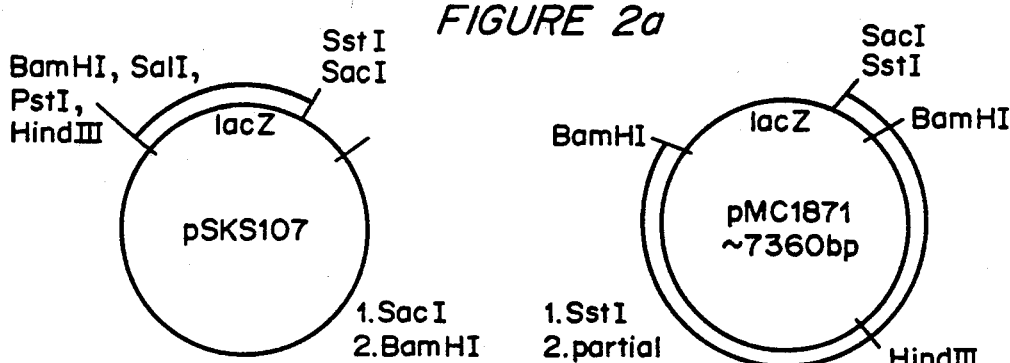
FIGURE 2a
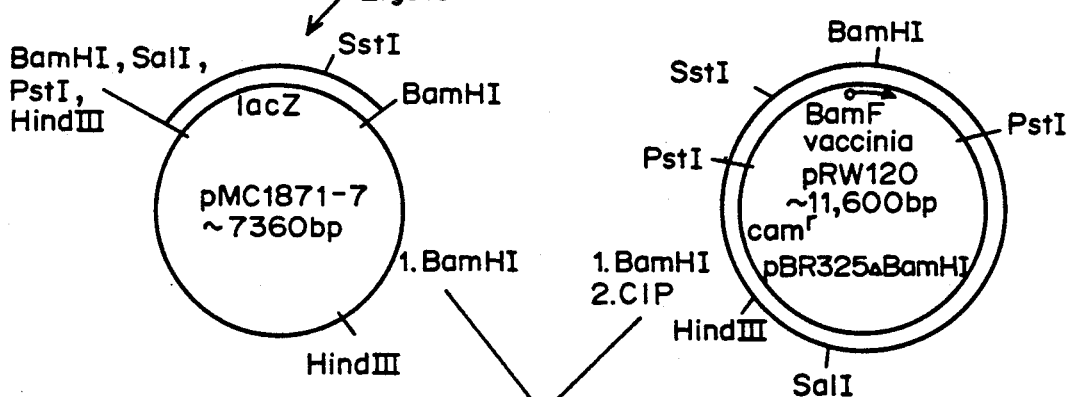
FIGURE 2b
FIGURE 2c
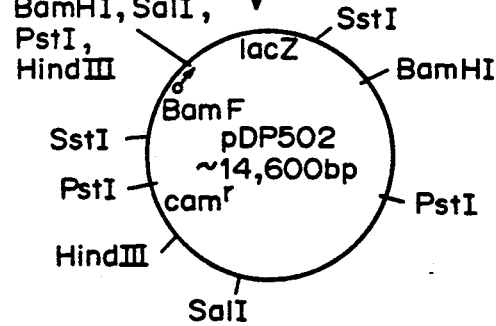
FIGURE 2d
Sequence at junction of vaccinia BamF and lacZ
TAAT<u>ATG</u>ACGCTCGTC<u>ATG</u>GGATCCGTCGACCTG---

*FIGURE 4a*
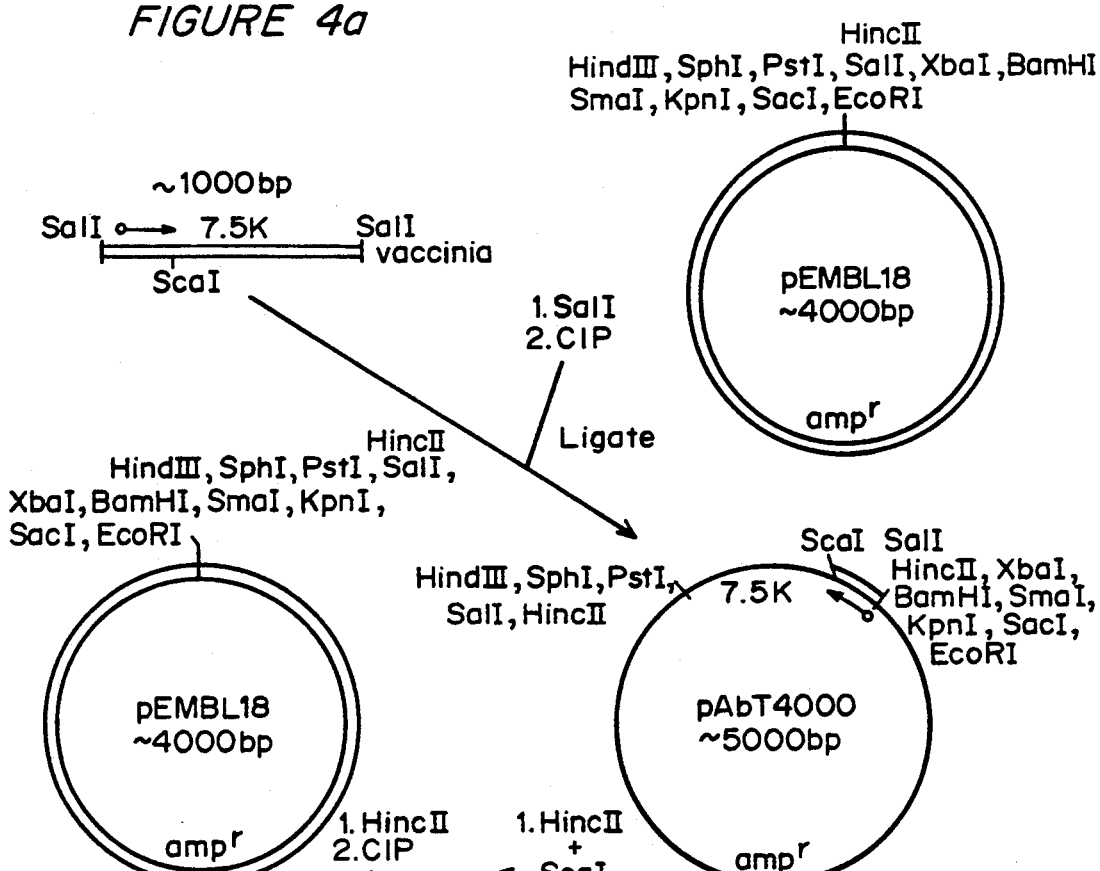
*FIGURE 4b*
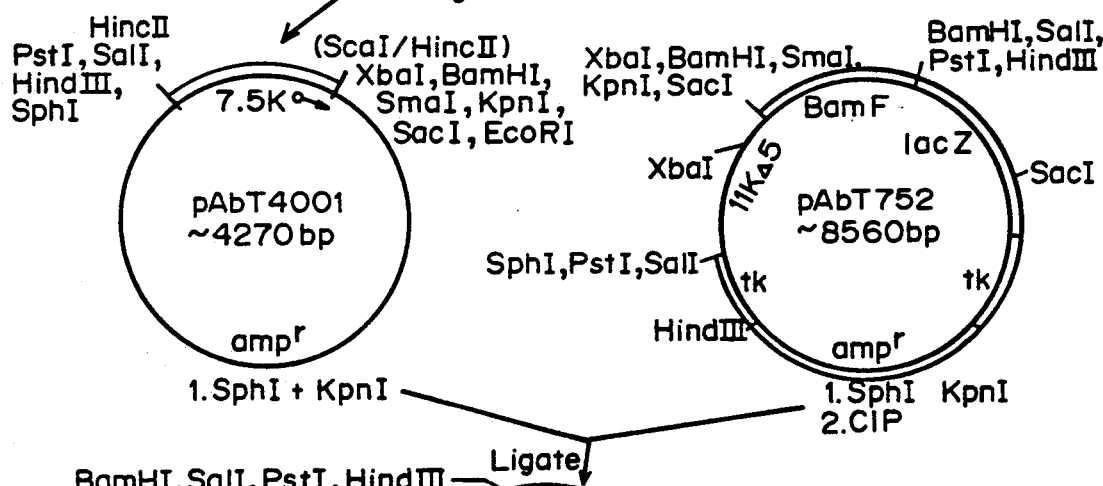
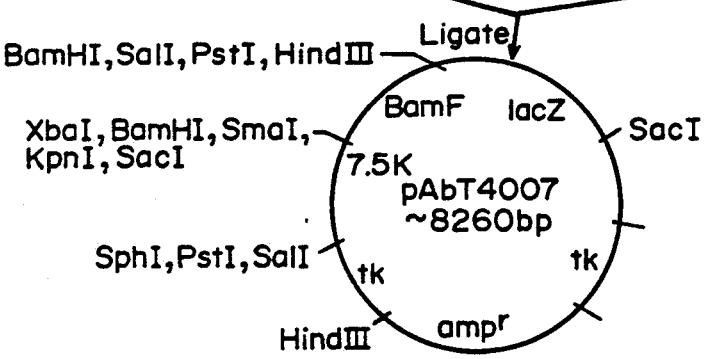
*FIGURE 4c*

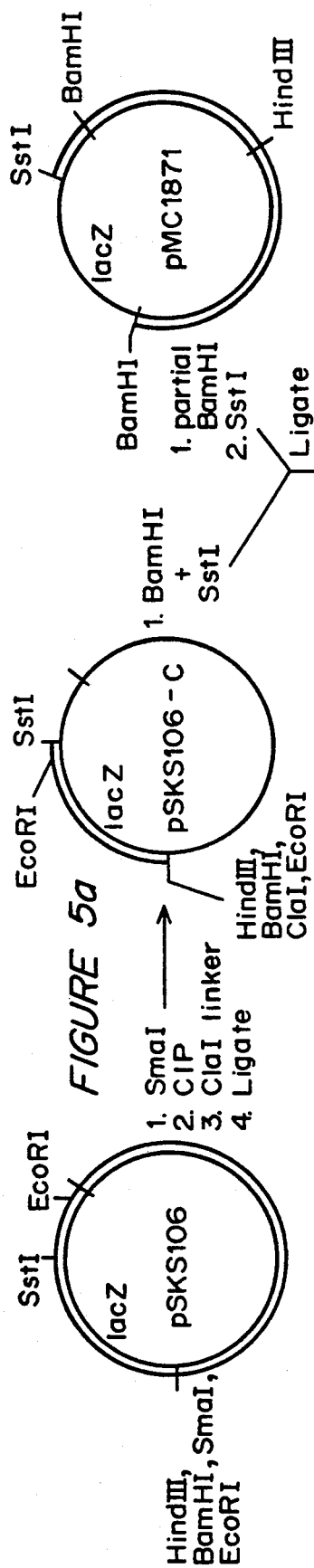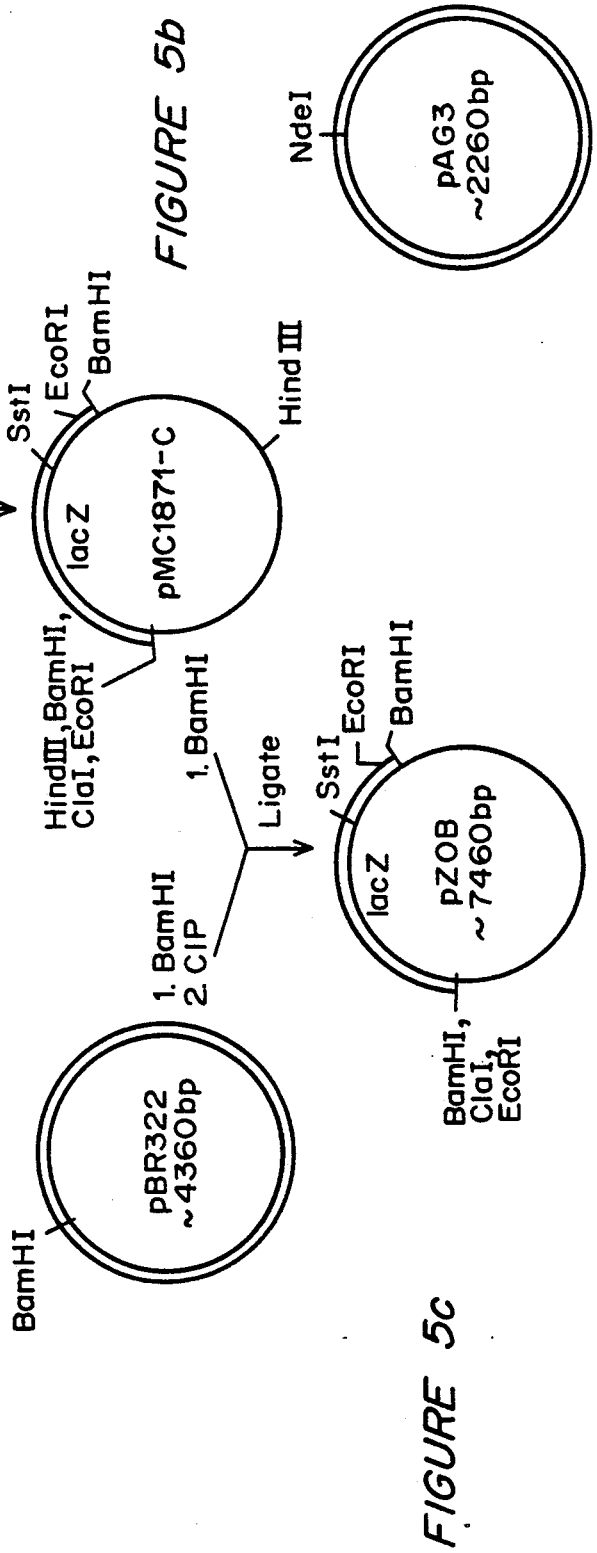

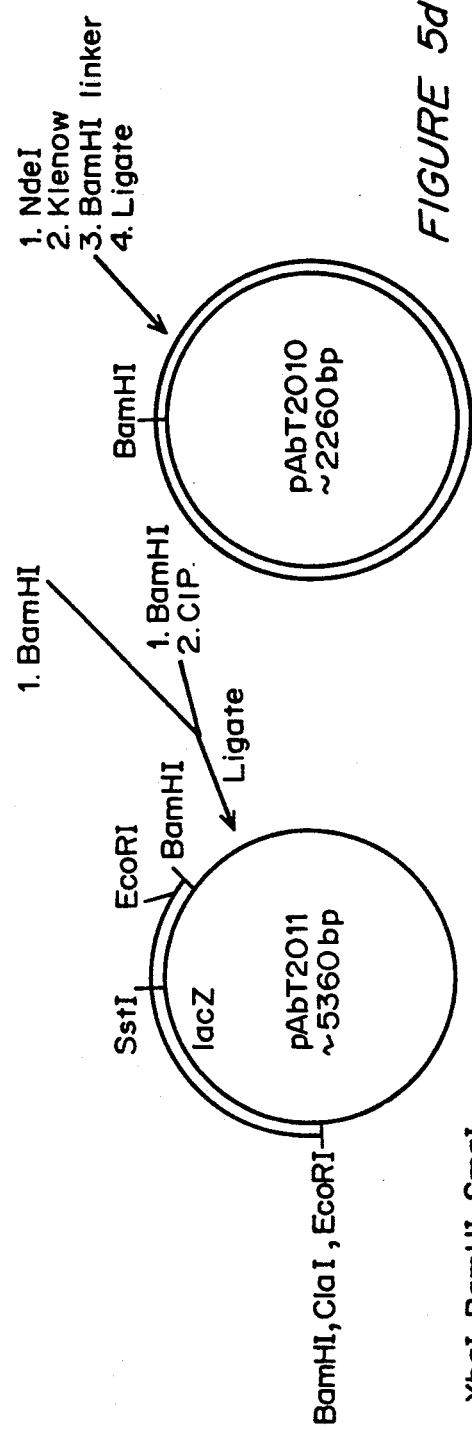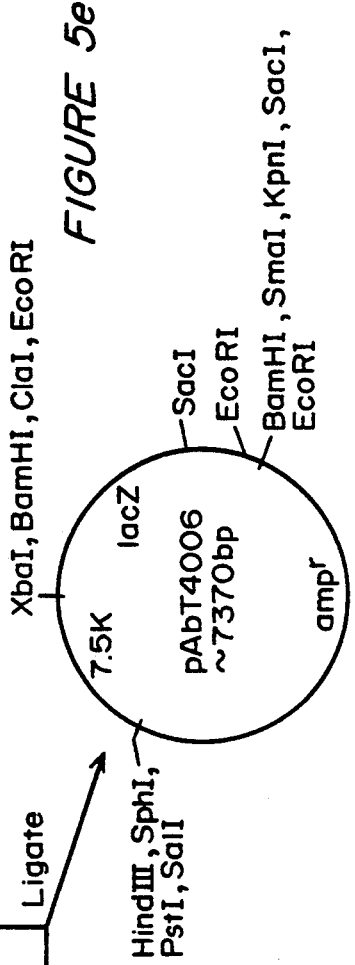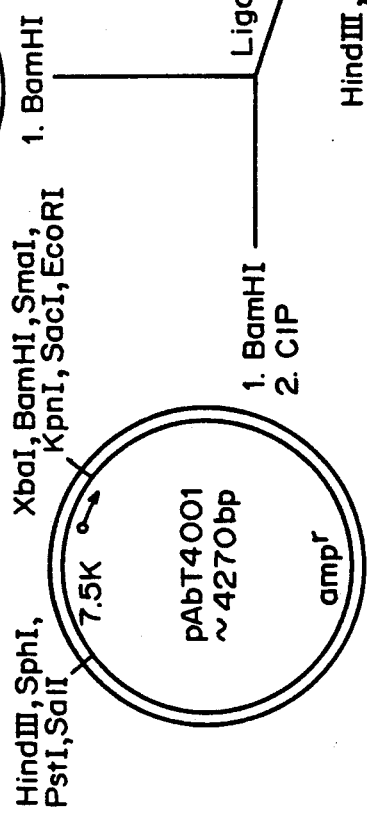
FIGURE 5d
FIGURE 5e

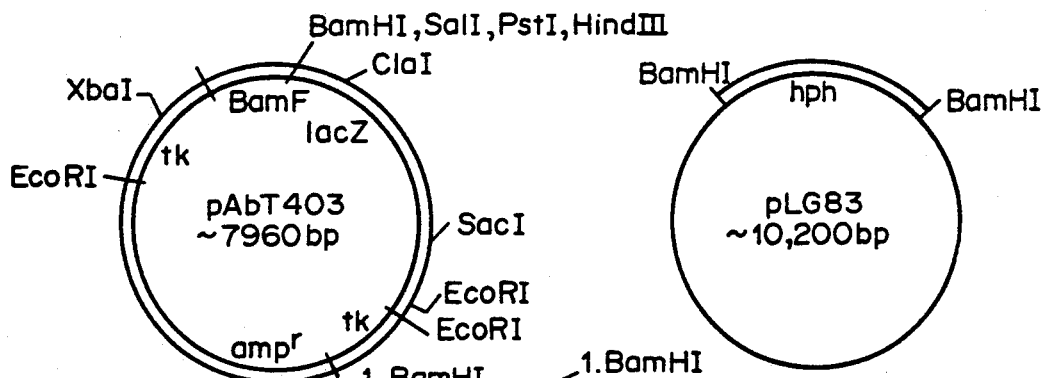
FIGURE 6a
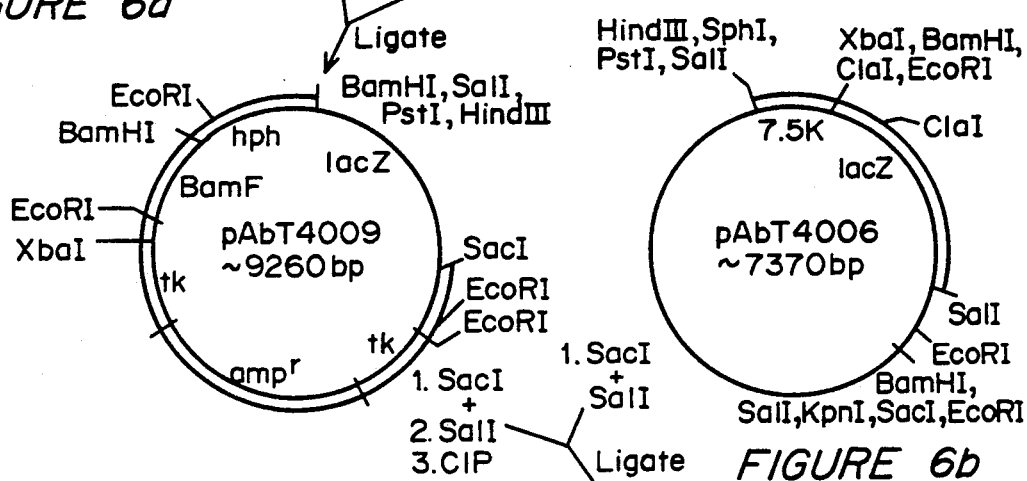
FIGURE 6b
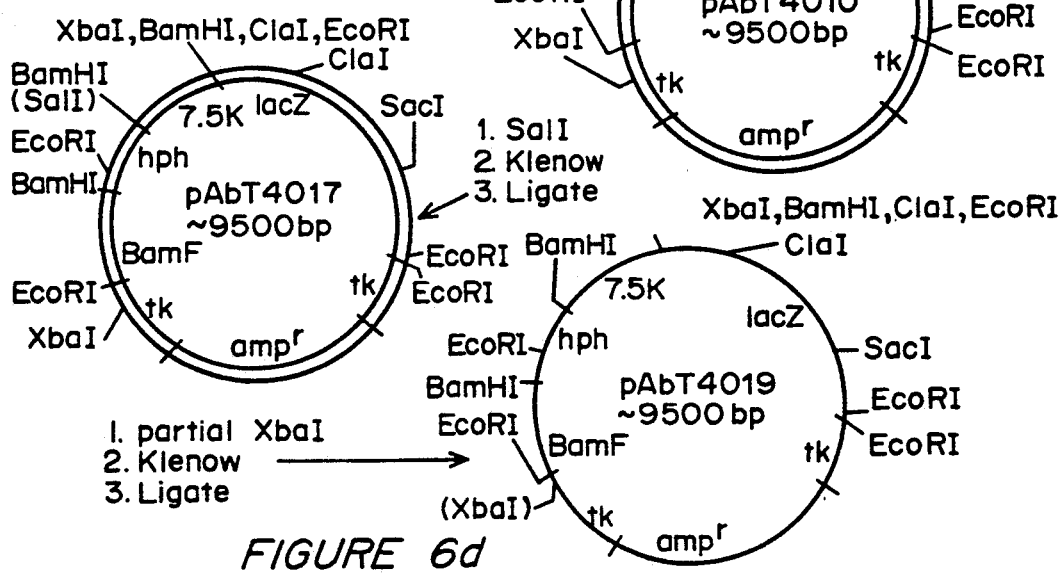
FIGURE 6c
FIGURE 6d

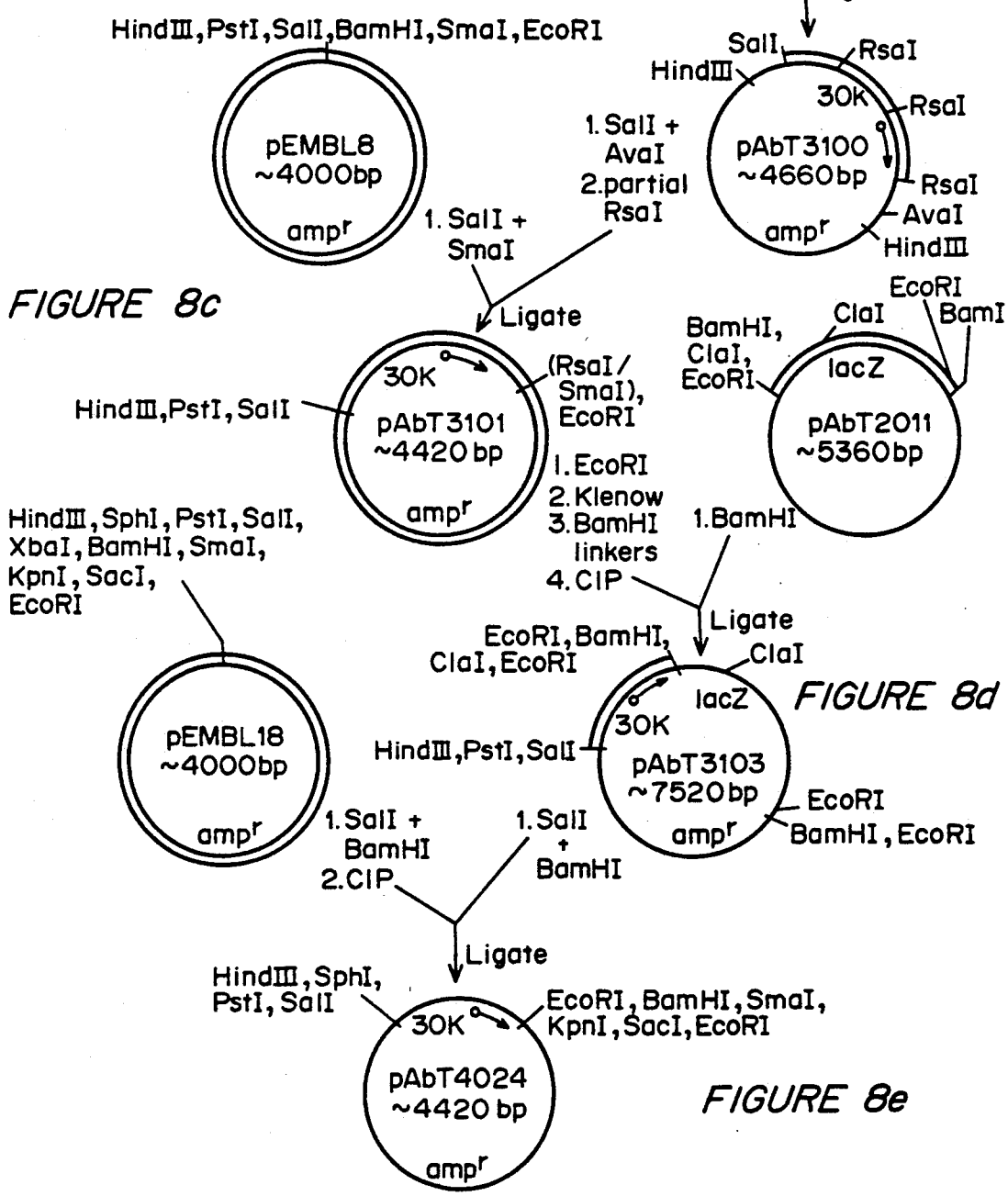

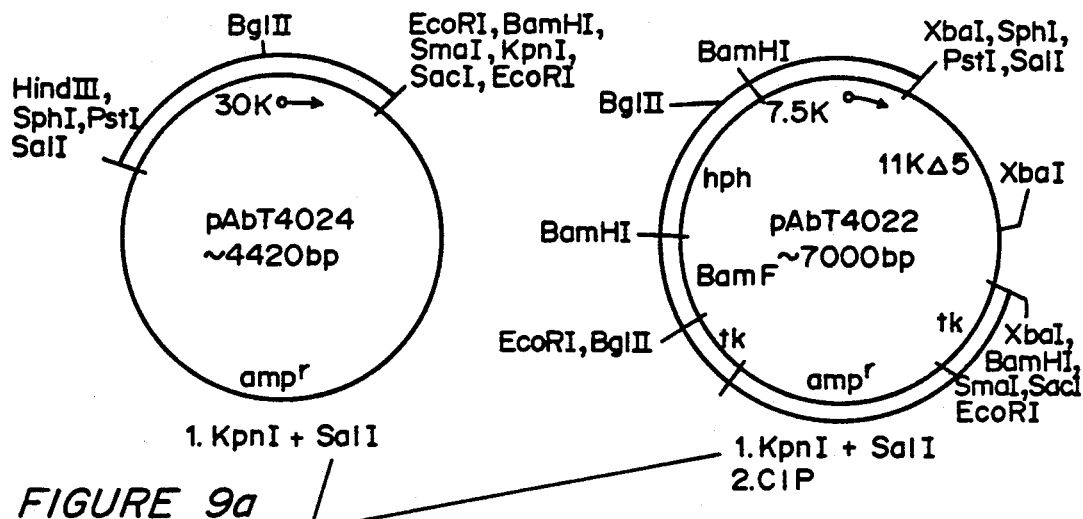
FIGURE 9a
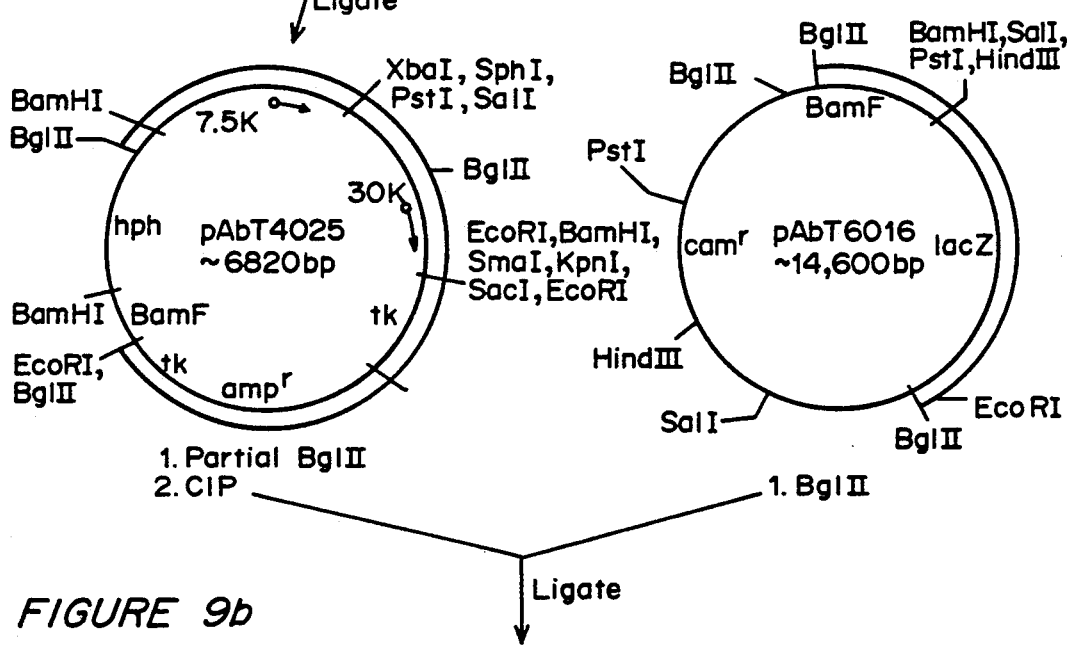
FIGURE 9b
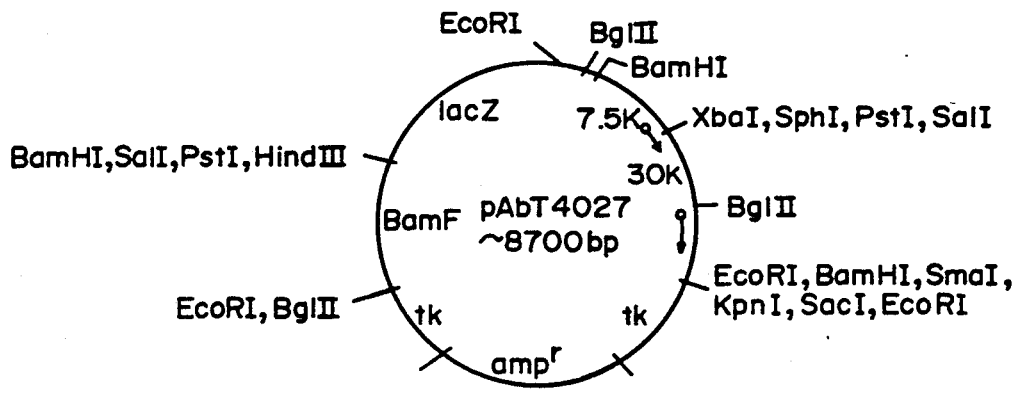

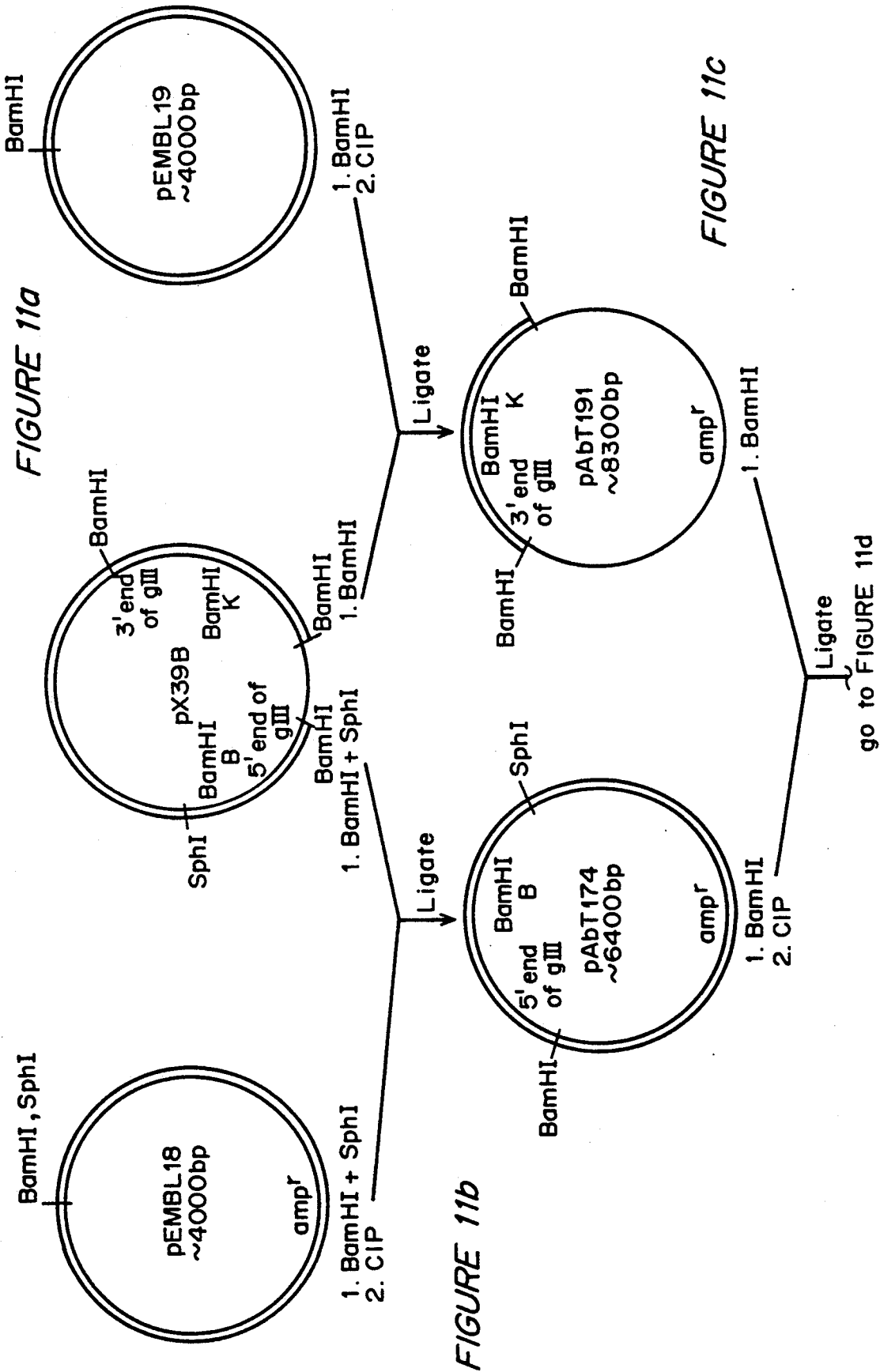

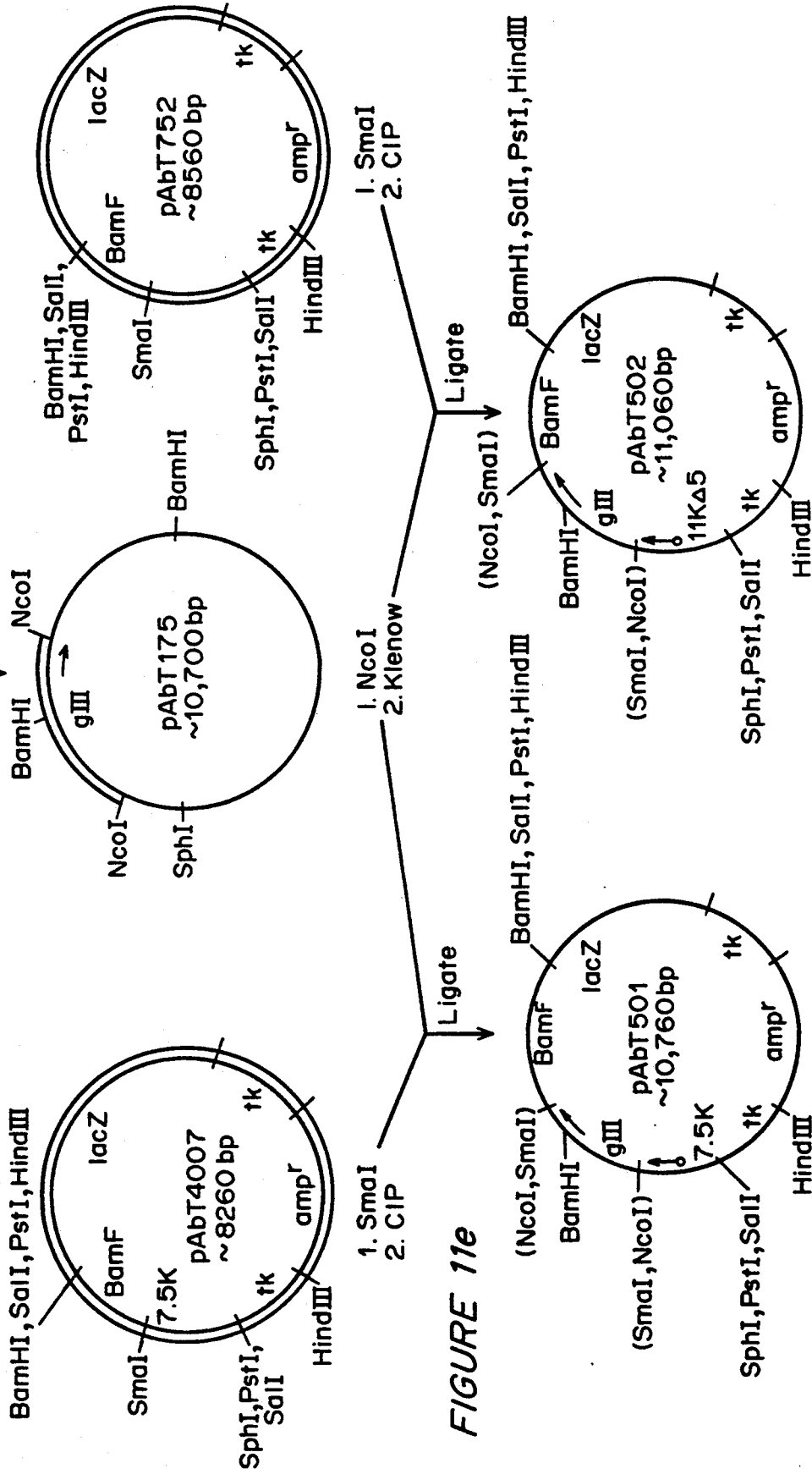

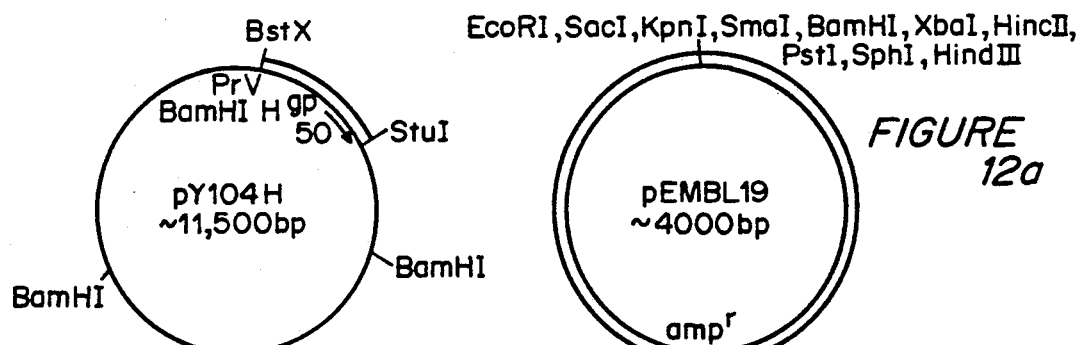
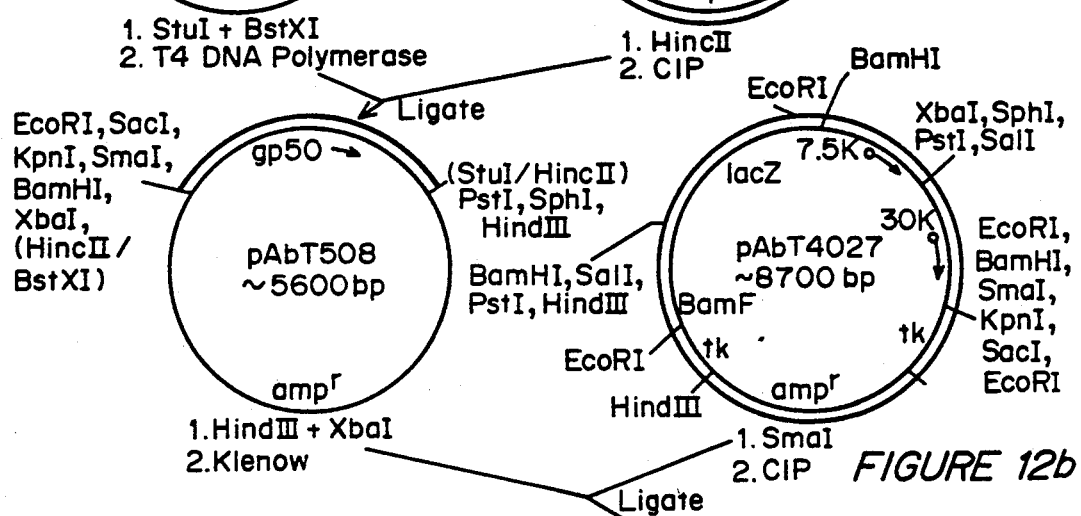
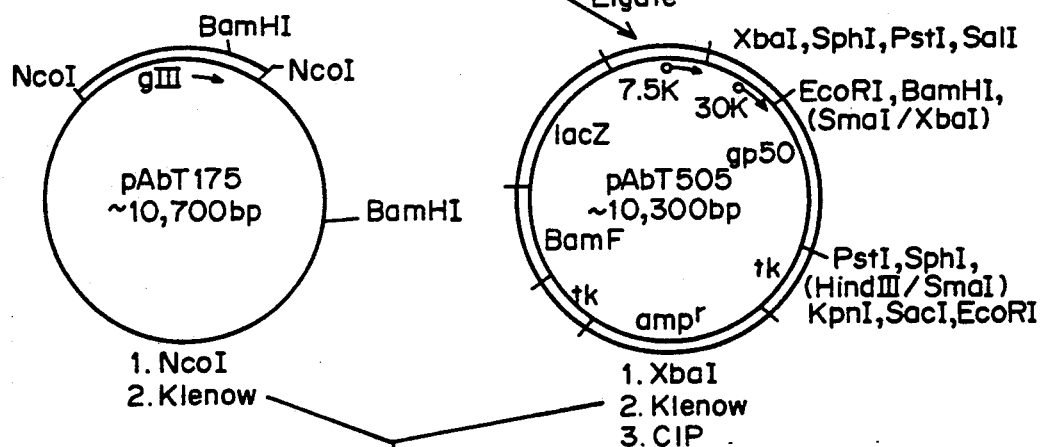
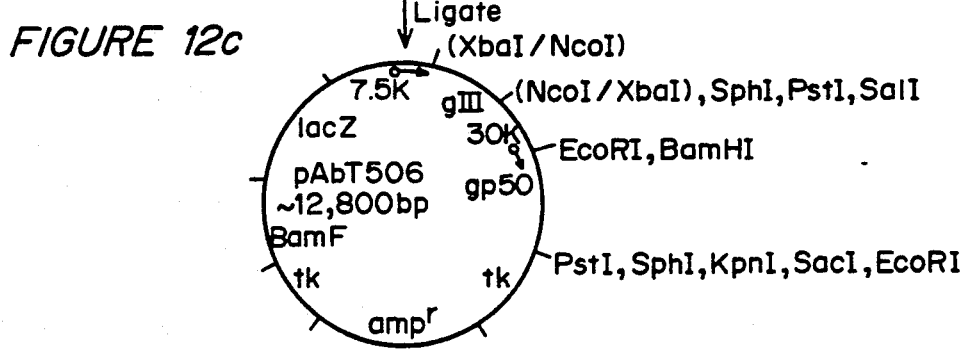

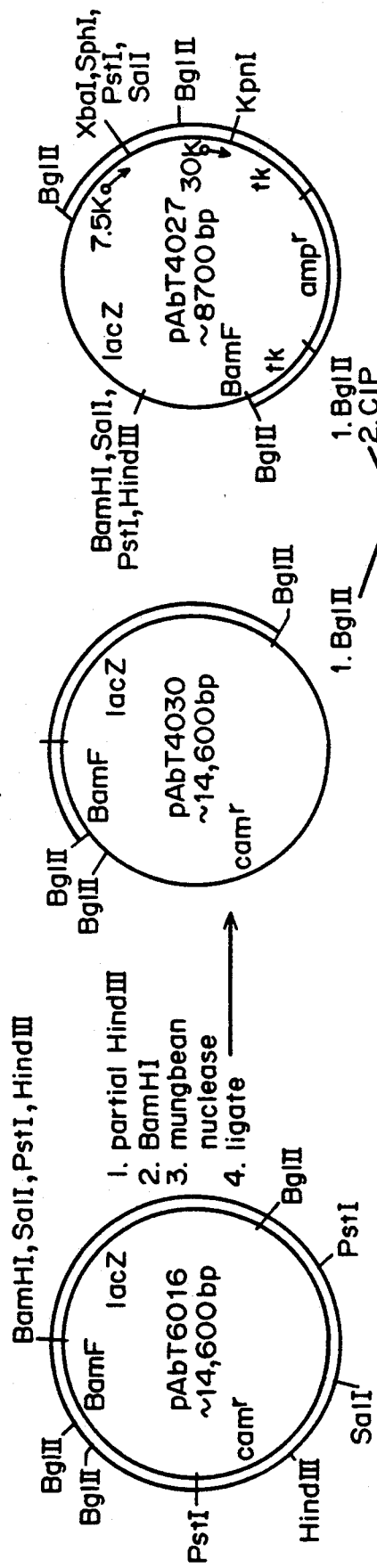
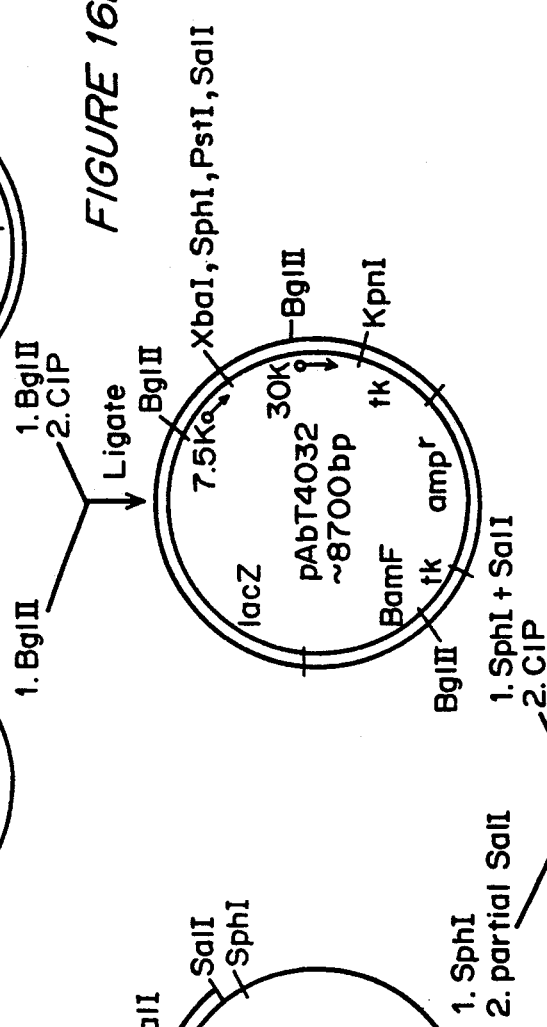
FIGURE 16a
FIGURE 16b

RECOMBINANT PSEUDORABIES VIRUS

This is a continuation of co-pending application Ser. No. 06/910,501 filed on Sep. 23, 1986, now abandoned.

BACKGROUND

Aujeszky's disease is a serious and often fatal respiratory and nervous system disease in swine, occurring worldwide. Young pigs are its major victims, but adults are susceptible and are also latent carriers of the virus, which can be passed to piglets. The disease is rare but usually fatal in sheep, goats, cattle, cats, and dogs.

The disease is caused by pseudorabies virus (PrV), also known as *Herpesvirus suis*. PrV consists of a linear, double stranded, $9 \times 10^7$ dalton molecule of DNA in a capsid surrounded by an envelope containing surface glycoproteins. The coding capacity of the PrV genome is 100 to 200 genes.

Current vaccines consist of inactivated or attenuated PrV; these reduce mortality but do not prevent latent infection. In theory, subunit vaccines, which would generally contain only immunogenic surface proteins of the virus, would be safer but perhaps not as effective. Protection against and recovery from infection by various pathogenic agents is determined by the host's immunological system. There are two interrelated but distinct immunological responses: humoral immunity, which is provided by circulating antibodies; and cellular immunity, provided by certain cells of the lymphoid system. Purified antigens alone, as in subunit vaccines, are sufficient to stimulate an antibody response in most cases; but they may not stimulate the cellular immune response which plays an equally or possibly more important role in prevention or recovery from infection. Live vaccines are the most effective means of stimulating both immunological responses. A need exists for live vaccine for PrV.

Vaccinia virus has been used in the worldwide eradication of smallpox. Its effectiveness in the vaccination program is due to its relative safety, stability, ease of administration and low cost. Vaccinia virus, a DNA virus, has several advantageous characteristics for use as a vector for creating live recombinant vaccines: they permit relatively easy genetic manipulation; they have a genome which can accept a large amount of foreign DNA; they are not oncogenic, are easy to grow and purify, and they have an extremely wide host range, infecting both man and animals.

Paoletti et al. (U.S. Pat. No. 4,603,112) have developed a technique known as in vivo recombination for integration of foreign DNA into vaccinia virus. Several foreign genes can be recombined into one virus using this technique, but each gene must be inserted individually.

A means of utilizing vaccinia virus as a eukaryotic vector has recently been developed. It has been demonstrated that foreign DNA sequences can be inserted into the genome of vaccinia virus by a process of site specific homologous recombination between replicating vacccinia genomes and appropriate vaccinia DNA sequences which flank the foreign DNA of interest (Panicali et al., Proc. Natl. Acad. Sci. USA. 1982. Vol. 79, pgs. 4927–4931). Recombinant viruses have been created in this manner to contain and express DNA sequences which code for proteins of pathogenic organisms.

SUMMARY OF THE INVENTION

This invention pertains to recombinant pox viruses capable of expressing immunogenic proteins of pseudorabies virus and to the use of these recombinant viruses for vaccination against pseudorabies virus and for the production of pseudorabies antigens. The invention also pertains to DNA vectors, into which a foreign gene or genes can be inserted, for recombination with pox virus to produce recombinant pox viruses which express the protein(s) encoded by the inserted DNA sequences. The vectors are used to produce mono or multivalent pox viruses. The divalent vectors allow two or more genes, from the same or different organisms, to be inserted together by a single in vivo recombination event. These vectors can be used to create monovalent and multivalent vaccinia virus containing and expressing the genes encoding the glycoproteins gp50, gII and gIII.

BRIEF DESCRIPTION OF THE FIGURES

FIGS. 1–3 show the construction of plasmid pAbT752. pAbT752 is a vector for in vivo recombination (IVR vector) with vaccinia virus; it contains the vaccinia thymidine kinase gene for directing the recombination, a lacZ gene under control of the vaccinia BamF promoter, the vaccinia 11KΔ5 promoter (a modified vaccinia 11K promoter) followed by a multiple cloning site for insertion of foreign genes and a bacterial replicon and the ampicillin resistance gene.

FIGS. 1 A–D show the construction of an intermediate plasmid (designated pAbT750) for formation of pAbT752 which contains the modified vaccinia 11K promoter 11KΔ5.

FIGS. 2 A–C show the construction of pDP502, another intermediate plasmid for formation of the plasmid pAbT752, which contains the vaccinia BamF promoter and the lacZ gene. FIG. 2D shows the sequence at the junction of the vaccinia BamF promoter and the lacZ gene in pDP502.

FIG. 3 (parts A and B) shows the final steps in construction of the IVR vector pAbT752 in which the 11KΔ5 and BamF-lacZ constructs of the intermediate plasmids pAbT750 and pDP502 are inserted within the vaccinia thymidine kinase gene.

FIGS. 4 A–C show the construction of the IVR vector pAbT4007 which has the same elements as pAbT752 except that it contains the vaccinia 7.5K promoter rather than the 11KΔ5 promoter.

FIGS. 5–7 show the construction of the divalent IVR vector pAbT4026. pAbT4026 contains the two vaccinia promoters 7.5K and 11KΔ5, each followed by unique multiple cloning sites for insertion of foreign genes.

FIGS. 5 A–E show the construction of pAbT4006, an intermediate plasmid in the construction of pAbT4026. pAbT4006 contains the 7.5 promoter and the lacZ gene.

FIGS. 6 A–D show the construction of pAbT4019, another intermediate plasmid in the construction of pAbT4026. pAbT4019 contains the vaccinia 7.5K promoter, the lacZ gene and the gene for hygromycin B phosphotransferase.

FIGS. 7 A–C show the final steps in the construction of pAbT4026.

FIGS. 8–9 show the construction of the divalent IVR vector pAbT4027 which has the same elements of pAbT4026 except that it contains the vaccinia 30K promoter rather than the 11K Δ5 promoter.

FIG. 8 (parts A-E) shows the construction of pAbT4024, an intermediate in the construction of pAbT4027, which contains the vaccinia 30K promoter.

FIGS. 9 A and B show the assembly of pAbT4027.

FIGS. 11 A-E show the construction of IVR vectors pAbT501 and pAbT502 each containing the pseudorabies gIII gene under the control of the vaccinia 7.5K and 11KΔ5 promoters respectively.

FIGS. 12 A-C show the construction of the divalent IVR vector pAbT506 containing the gIII gene under the control of the vaccinia 7.5K promoter and the gp50 gene under the control of the 30K promoter.

FIGS. 15 A-D show the construction of pAbT780, an intermediate in the construction of pAbT781, which contains the 5' end of the gII gene.

FIGS. 16 A-E show the final steps in the construction of pAbT781.

DETAILED DISCLOSURE OF THE INVENTION

Figures 1D, 1E:
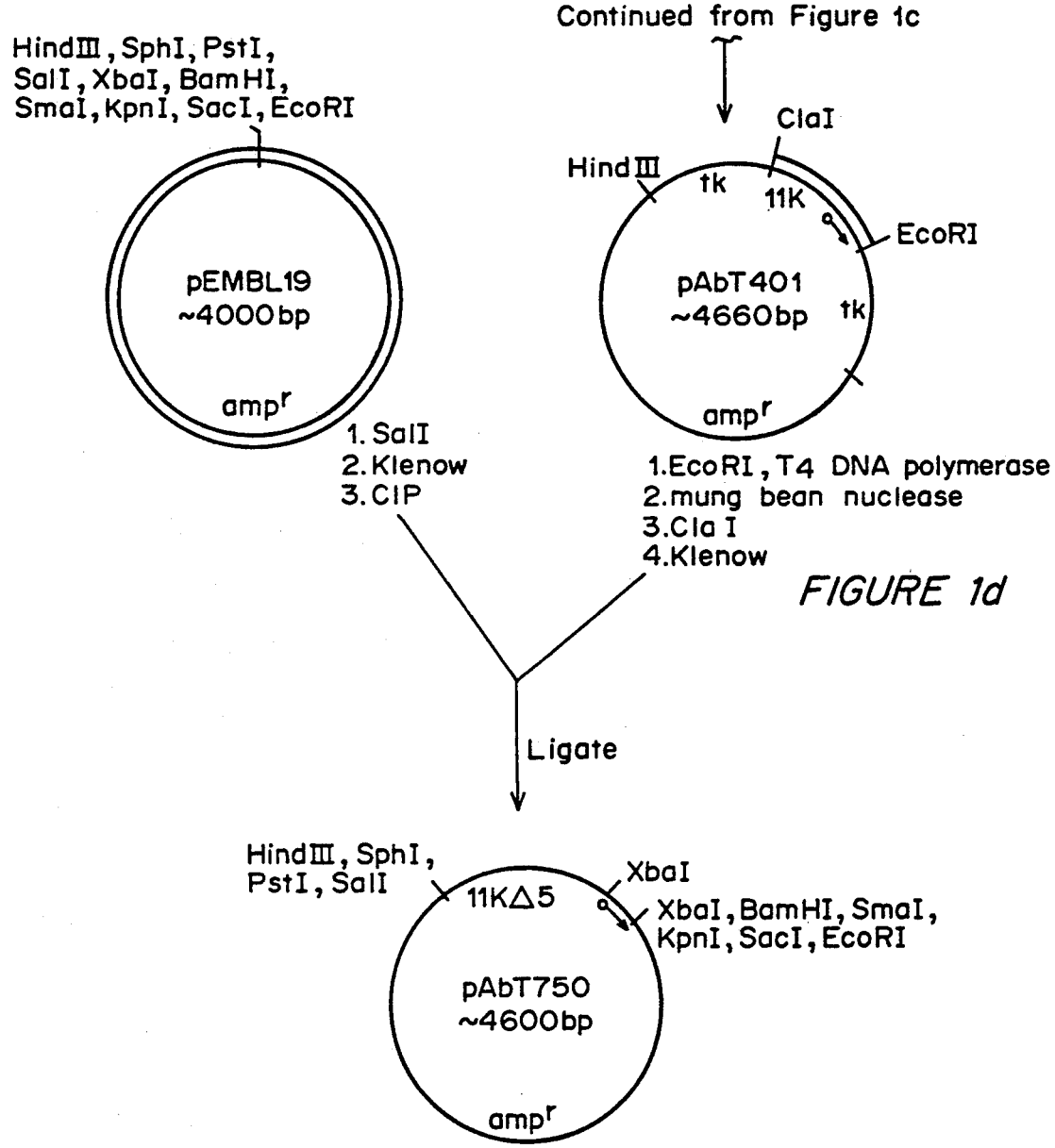
FIG. 1E shows the sequence of the 11K promoter and the sequence of 11KΔ 5-pEMBL19 junction of pAbT750.

1 Genes for Integration into Pox Virus

Foreign genes for integration into the genome of a pox virus in expressible form can be obtained by any conventional technique for isolating a desired gene. The genes can be derived from organisms, including bacteria, viruses or other microorganisms, for which a pox virus based live vaccine is desired. For purposes of a vaccine, genes of interest are those which encode immunogenic proteins of an organism. In many cases, these are protein components of surface structures such as the bacterial cell wall or viral envelope. In appropriate instances, immunogenic fragments or subunits of the proteins may be used.

For organisms which contain a DNA genome, the genes encoding an antigen of interest are isolated from the genomic DNA; for organisms with RNA genomes, the desired gene may be isolated from cDNA copies of the genome. If restriction maps of the genome are available, strategies can be designed for cleaving genomic DNA by restriction endonuclease digestion, to yield DNA fragments that contain the gene of interest. In some cases, desired genes may have been previously cloned and thus, the genes can be obtained from the available clones. Alternatively, if the DNA sequence of the gene is known, the gene can be synthesized by any of the conventional techniques for synthesis of deoxyribonucleic acids (e.g., the phosphate or phosphite triester techniques).

Depending on the design of the vector, genes can be isolated or synthesized with or without the endogenous translational start signal ATG. The resulting antigen can be expressed as a protein identical to the protein made in the original organism either by using its entire coding sequence including its own translation start codon ATG or, if containing all codons except its start codon, by ligating to an ATG codon provided by the vector. The antigen can also be expressed as a fusion protein with its N- or C-terminus encoded by another gene. For example, some prokaryotic genes contain the translation initiation codon GTG which is not functional in eukaryotic systems. In these cases, the gene can be expressed in eukaryotes by fusion, in the correct reading frame, to an ATG. Fusions can be made to other genes in order to direct the localization of the resulting fusion protein in the organism or to provide for secretion of the protein into the medium outside of the organism. In addition, fusions can be made in order to alter or enhance the immunogenicity of a protein.

Genes encoding an antigen of interest can be amplified by cloning the gene into a bacterial host. For this purpose, various prokaryotic cloning vectors can be used. Examples are plasmids pBR322 and pEMBL.

The genes encoding the antigen of interest can be prepared for insertion into the DNA vectors designed for recombination with pox virus by standard techniques. In general, the cloned genes can be excised from the prokaryotic cloning vector by restriction enzyme digestion. In some cases, the excised fragment will contain the entire encoding region of the gene, including its translational start signal; in others, the translational start signal will be absent. The DNA fragment carrying the cloned gene can be modified as needed, for example, to make the ends of the fragment compatible with the insertion sites of the DNA vectors used for recombination with poxvirus, then purified prior to insertion into these vectors at restriction endonuclease cleavage sites (cloning sites) as described below.

As described in more detail below, the genes encoding pseudorabies virus glycoproteins gp50, gII or gIII were isolated from the genomic DNA of pseudorabies virus and cloned into *E. coli* plasmid vectors. After amplification, the protein-encoding region of each gene, including its translational start signal, were excised from the bacterial plasmid by restriction endonuclease cleavage and inserted into the pox recombination vectors. Other examples of pseudorabies virus glycoproteins which can be inserted into pox virus include gI, gp63, and gX (gp100).

2. Pox Viruses

Any member of the pox family can be used for the generation of recombinant viruses; for the purposes of vaccine development, the preferred pox virus is a virus which does not cause significant disease in normal humans or animals. For example, for humans and other mammals, the preferred pox virus is vaccinia virus, a relatively benign virus, which has been used for years as a vaccine against smallpox. Several strains of vaccinia, which differ in level of virulence, are available for use as vaccine strains; for the purposes of vaccination, a less virulent strain such as the New York City Board of Health Strain which still retains the ability to elicit an appropriate immune response is preferred. As another example, for vaccination of poultry, fowl pox virus may be the preferred vaccine strain. General techniques for integration of foreign DNA into vaccinia virus to produce a modified virus capable of expressing foreign protein encoded by the foreign DNA are described by Paoletti et al. U.S. Pat. No. 4,603,112, the teachings of which are incorporated by reference herein.

3. DNA Vectors for Recombination with Pox Virus

According to the method of this invention foreign genes which encode immunogenic proteins are inserted into the genome of a pox virus so as to allow them to be expressed by the pox virus along with the expression of the normal complement of pox virus proteins (except for the pox viral protein encoded by the gene into which the foreign DNA is inserted). This is accomplished by first constructing a DNA vector for recombination with pox virus which contains the foreign gene or genes of interest flanked by pox viral sequences. The flanking pox viral sequences can be any pox DNA region nonessential for replication; these allow the vector to recombine with pox virus in vivo at a specific region in the pox virus genome. This recombination results in integration of the foreign DNA into the genome to produce a recombinant virus containing the foreign gene or genes.

The DNA vectors of this invention for integration of a foreign gene in expressible form into the pox viral genome contain the following elements:

a. a pox viral promoter linked to:

b. a DNA sequence containing a multiple cloning site for insertion of foreign DNA;

c. DNA sequences flanking the construct of elements a and b, the flanking sequences being homologous to a region of the pox viral genome which is nonessential to replication of the virus;

d. a replicon for vector replication in a prokaryotic host; and e. a gene encoding a selectable marker or indicator for selection of the vector in transformed prokaryotic hosts.

The multiple cloning site comprises recognition sites for several restriction enzymes which allow different modes of insertion of foreign DNA. An example sequence containing a multiple cloning site is: GGATCCCCGGGTACCGAGCTCGAATTC, which contains the recognition sequences and cleavage sites for the restriction endonuclease enzymes BamHI, SmaI, KpnI, SacI and EcoRI. Sequences containing additional or different recognition sites can be used. The cloning site is located adjacent to and downstream of a pox viral promoter such that an inserted gene can be placed under control of the promoter.

The pox viral promoter controls expression of the foreign gene inserted at the cloning site and can be obtained from the species of pox virus with which the vector is designed to recombine.

The sequences flanking the construct of elements a and b (the pox viral promoter and adjacent cloning site) are homologous to a region of the pox viral genome which is not necessary for replication of the pox virus. Thus, recombination and integration of foreign DNA will occur at this site and the inserted DNA will not abolish viral replication. A preferred region for insertion into pox virus is within the gene coding for thymidine kinase (TK). Insertion into this region has several advantages: (1) as discussed above, the TK gene is not required for viral replication, so insertions into this gene do not abolish viral replication; (2) insertions into the TK gene do, however, partially inhibit viral replication, resulting in a recombinant pox virus that is less virulent and therefore possibly more suitable as a vaccine strain; and (3) it is possible to select recombinant viruses by selecting for insertional inactivation of the TK gene by growth in the presence of 5-bromodeoxyuridine. In order to obtain insertion into the TK gene, the recombination vector must contain flanking sequences homologous to the TK gene sequences.

Other non-essential regions of the pox virus genome can be used as flanking sequences to direct the stable integration of the DNA vector into the pox virus genome; these include, but are not limited to, regions of the genomic DNA contained on the HindIIIM restriction fragments.

The replicon for replication in a prokaryotic host and the gene encoding the selectable indicator or marker allow the vector to be selected and amplified in a prokaryotic host such as $E.\ coli$ to provide ample quantities of the vector DNA for eventual transfection of eukaryotic host cells for recombination. The replicon can be obtained from any conventional prokaryotic vector such as pBR322 or pEMBL. The selectable marker can be a gene conferring antibiotic resistance (e.g. ampicillin, chloramphenicol, kanamycin or tetracycline resistance).

Preferred vectors contain genetic elements which permit positive selection of recombinant viruses, i.e., those viruses which have recombined with the vector and, as a result, have acquired the foreign gene or genes. These elements comprise a gene encoding a selectable marker or indicator and a pox virus promoter, which controls expression of the gene in the recombinant virus. The promoter and marker or indicator gene are located between the flanking pox viral sequences so that the elements which allow for selection and the foreign gene of interest are co-integrated into the pox viral genome. Recombinant viruses can then be selected based upon expression of the marker or indicator.

A preferred gene for selection is the $E.\ coli$ lacZ gene which encodes the selectable enzyme B-galactosidase. Methods of selection based upon expression of this enzyme are discussed below. Other selection methods include thymidine kinase selection as described above, and any drug resistance selection, for example, the selection that is provided by the gene encoding neomycin phosphotransferase, an enzyme which confers resistance to G418 (Franke et al., 1985. Mol. Cell. Biol. 5, 1918).

As mentioned above, the preferred species of pox virus for insertion of foreign genes for production of vaccines is the vaccinia species. Accordingly, preferred vectors are designed for recombination with the vaccinia virus and thus, the pox viral elements of the vector are derived from vaccinia virus. A vector for recombination with vaccinia virus can contain:

a. a vaccinia promoter (e.g. the vaccinia 11K, 7.5K or 30K promoter or modified versions of these promoters);

b. a multiple cloning site adjacent to the promoter;

c. a second vaccinia promoter (e.g. the vaccinia BamF promoter);

d. a gene encoding a selectable marker (e.g. the $E.\ coli$ lacZ gene);

e. DNA sequences homologous to a region of vaccinia virus nonessential for replication of the virus, the DNA sequences flanking the construct of elements a–d (e.g., sequences of the vaccinia thymidine kinase gene);

f. a replicon for replication in a bacterial host; and g. a gene encoding a selectable marker under control of a prokaryotic promoter for selection of the vector in a prokaryotic host.

Vaccinia promoters are DNA sequences which direct messenger RNA synthesis from vaccinia genes during a vaccinia virus infection. Such promoters can be isolated from the vaccinia genome or can be constructed by DNA synthesis techniques. Promoters vary in strength of activity and in time of expression during the vaccinia virus life; these parameters can be altered by mutation of the promoter sequence. The promoters can be isolated or synthesized to include or not include a translational initiation codon ATG as well as a multiple cloning site for convenient insertion of foreign genes in order to express these genes in vaccinia.

With current technology, two or more foreign genes can be inserted into vaccinia virus by several in vivo recombination events; that is, each gene must be inserted individually. This invention also provides for the insertion of two or more foreign genes by a single in vivo recombination event.

For this purpose, vectors are provided for introduction of two or more foreign genes into pox virus. These vectors can be employed to produce recombinant pox viruses which express two or more different antigenic proteins to provide multivalent vaccines. The proteins can be derived from one or more organisms. Vectors for introduction of multiple foreign genes into pox virus contain the elements as described above for a monovalent vector and one or more additional pox viral promoters, each followed by a multiple cloning site for insertion of one or more additional genes encoding immunogenic proteins of one or more organisms. The additional promoter(s) and multiple cloning site(s) are located between the flanking pox viral sequences which direct recombination in the pox virus. A vector for introduction of two or more foreign genes into a vaccinia virus can comprise any combination of two, three or more of the various vaccinia promoters, each followed by a multiple cloning site for selective insertion at each site of a different gene of interest. For example, a divalent vector can contain:

a. a first vaccinia promoter followed by a multiple cloning site appropriately situated so that any inserted gene is controlled by the promoter;

b. a second vaccinia promoter and adjacent cloning site; and c. a third vaccinia promoter linked to a gene encoding a selectable marker or indicator.

This construct is flanked by sequences of vaccinia which direct recombination. Preferably, the first, second, and third vaccinia promoters are different promoters. There are several advantages to using different promoters in one vector. Different promoters may have varying strengths of activity and different times of expression during the vaccinia virus life cycle. The parameters for optimal expression of different antigens may vary with each antigen and therefore different promoters may be optimal. Also, repeated DNA sequences located near each other are unstable in vaccinia virus. The use of the same promoters in one vector would produce closely linked repeated DNA sequences in the recombinant vaccinia virus and thus may result in instability. Different promoters have different DNA sequences and therefore would be stable when recombined into the same region of the vaccinia genome.

Because of the convenient multiple cloning sites, any isolatable gene(s) can be easily inserted into these monovalent and divalent in vivo recombination vectors. In this invention, the genes encoding pseudorabies virus glycoproteins gp50, gII and gIII have been put under the control of the 7.5K, 11K and/or 30K promoters by insertion into the multiple cloning sites of several monovalent and divalent vectors for in vivo recombination in vaccinia.

4. In vivo Recombination

The intermediate DNA vectors containing the gene of interest (and the marker or indicator gene) flanked by appropriate pox viral sequences will undergo recombination with pox virus which results in integration of the flanked genes into the pox viral genome. This recombination will occur in a eukaryotic host cell. Appropriate host cells for recombination are cells which are 1) infectable by pox virus and 2) transfectable by the DNA vector. Examples of such cells are chick embryo fibroblast, CV-1 cells (monkey kidney cells), HuTK−143 cells (human cells), and BSC40 cells.

The cells are first infected with pox virus and then transfected with the intermediate DNA vector. Viral infection is accomplished by standard techniques for infection of eukaryotic cells with pox virus. See e.g., Paoletti et al., supra. The cells can be transfected with the intermediate DNA vector by any of the conventional techniques of transfection. These include the techniques of calcium phosphate precipitation, DEAE dextran, electroporation and protoplast fusion. The preferred technique is the calcium phosphate precipitation technique.

After infection and subsequent transfection, the cells are incubated under standard conditions and virus is allowed to replicate during which time in vivo recombination occurs between the homologous pox virus sequences in the intermediate vector and the pox virus sequences in the genome.

Recombinant viral progeny are then selected by any of several techniques. The presence of integrated foreign DNA can be detected by hybridization with a labeled DNA probe specific for the inserted DNA. Alternatively, virus harboring the foreign gene can be selected on the basis of inactivation of the viral gene into which the foreign DNA was inserted. For example, if the DNA vector is designed for insertion into the thymidine kinase (TK) gene of a pox virus, viruses containing integrated DNA will be unable to express thymidine kinase (TK−) and can be selected on the basis of this phenotype. Preferred techniques for selection, however, are based upon co-integration of a gene encoding a marker or indicator gene along with the gene of interest, as described above. A preferred indicator gene is the *E. coli* lacZ gene which encodes the enzyme B-galactosidase. Selection of recombinant viruses expressing B-galactosidase can be done by employing a chromogenic substrate for the enzyme. For example, recombinant viruses are detected as blue plaques in the presence of the substrate 5-bromo-4-chloro-3-indolyl-B-D-galactoside or other halogenated-indolyl-B-D-galactosides (BluoGal TM).

The monovalent and divalent in vivo recombination vectors containing the genes encoding pseudorabies virus glycoproteins gII or gp50 and/or gIII were recombined into vaccinia at the TK gene and recombinants were selected as blue plaques using the lacZ gene and BluoGal TM substrate. Expression of the proteins encoding these pseudorabies glycoproteins in the vaccinia recombinants was confirmed by various immunological methods.

5. Vaccines

Live recombinant viruses expressing immunogenic proteins from one or more pathogens can be used to vaccinate animals susceptible to these pathogens. These vaccines may be administered intradermally, as was conventionally done for small pox vaccination, or by other routes appropriate to the recombinant virus used and the disease for which protection is desired. These may include among others, intramuscular, subcutaneous, and oral routes. Vaccination of a host organism with live recombinant vaccinia virus is followed by replication of the virus within the host. During replication, the foreign gene is expressed along with the normal complement of vaccinia genes. If the foreign gene product is an antigen, it will stimulate the host to mount an immunological response, both humoral and cell mediated, to the foreign antigen as well as to vaccinia virus itself. If the foreign antigen can stimulate protein immunological response, then the host animal will be immune to infection by the corresponding pathogenic agent.

Several recombinant vaccinia viruses expressing foreign antigens have been constructed and used as live vaccines. These viruses have elicited, in host animals, both humoral and cell mediated responses to the foreign antigen and have protected the animal against subsequent challenge with the virulent pathogens. (Paoletti et. al., 1984 Proc. Natl. Acad Sci, U.S.A. vol. 81, p.193-197; Moss et al. 1984 Nature. vol. 311,p67-69; Wiktor et. al. 1984. Proc Natl. Acad. Sci. U.S.A. vol. 81, p. 7194-7198; Elango et. al. Proc. Natl. Acad. Sci. U.S.A. vol 83, p.1906-1910.)

Live recombinant vaccinia viruses containing and expressing one or more of the genes encoding pseudorabies virus glycoproteings gp50, gII, and gIII (or other immunogenic proteins of pseudorabies virus) provide monovalent and divalent vaccines for immunizing swine and other animals against Aujeszky's disease.

An additional advantage of utilizing recombinant pox viruses as live vaccines is that they express only selected antigens, preferably only those antigens sufficient to elicit a protective response. It is therefore possible to differentiate between host animals which have been vaccinated with the recombinant pox virus and those which have been infected with the authentic, virulent, disease-causing agent.

The vaccinated host will develop antibodies only to the pox virus and to the selected foreign antigen(s). By contrast, the actively infected host will generate a full complement of antibodies directed toward the pathogenic agent, including antibodies directed to specific antigens not present in the recombinant pox virus. The presence of these additional antibodies, which can be detected using appropriate immunological tests (e.g., ELISA), is therefore diagnostic of a naturally occuring infection of the host with the pathogen.

Using this invention, recombinant vaccinia viruses containing selected pseudorabies antigens can be used as vaccines. Because vaccinated animals will produce antibodies against only those pseudorabies antigens expressed by the recombinant vaccinia virus used for vaccination, they can be distinguished from animals infected with the pseudorabies virus; the infected animals, in contrast to vaccinated animals, will contain antibodies to the entire complement of pseudorabies antigens.

Recombinant pox viruses expressing foreign antigens can also be used to generate immunogenic proteins in culture which can be used as subunit vaccines. Antigens for subunit vaccine preparations can be produced by infecting eukaryotic cell cultures with one or more recombinant viruses, each expressing one or more foreign antigens. The infected cell will express these foreign antigens along with the complement of pox virus proteins. These antigens can then be utilized as a subunit (non-live) vaccine preparation. The foreign anti-gens may be purified from the infected cells for administration or they may be given as a crude lysate of infected cells. Under these circumstances, any live recombinant pox viruses present would have to be inactivated, which can be done by conventional techniques such as the use of formalin, heat, and ultra violet radiation, among others.

For example, subunit vaccines can be made from the monovalent and divalent recombinant vaccinia viruses containing the genes encoding pseudorabies glycoproteins gp50, gII, gIII, or other pseudorabies proteins.

6. Diagnostic Uses of Recombinant Pox Viruses

Recombinant pox virus which express one or more foreign antigens can also provide diagnostic tools for detection of the organism which normally contains these antigens. Infection of experimental animals with the recombinant pox viruses can be used to raise both monoclonal antibodies and polyclonal antisera which recognize the specific epitopes of the foreign protein. These monoclonal and/or polyclonal antibodies can be used individually or together as capture antibody for immunoassay in the RIA or ELISA format, to detect the present in a biological fluid (e.g., urine, blood, or feces) of the organism which normally contains these antigens.

Alternatively, cells infected in vitro with the recombinant pox viruses can be used as a source of the foreign antigen produced by the recombinant viruses for an immunoassay to detect the presence of antibody in urine, blood, or feces of an animal. Particularly preferred immunoassays are solid phase immunometric assays (enzymetric or radiometric). In such assays, the antigen of interest is immobilized on a solid phase to provide an immunoadsorbent. The immunoadsorbent is then incubated with a sample of bodily fluid to be tested under conditions sufficient for antibody reactive with the antigen to complex with immobilized antigen. The immunoadsorbent is separated from the sample and antibody associated with the immunoadsorbent is detereined as an indication of the level in the sample of antibody against the organism which normally contains the antigen. Antibody bound to the immunoadsorbent is generally determined by incubating the immunoadsorbent with a labeled (radioisotopically or enzymatically) antibody against antibody of the species from which the sample is derived and detecting label associated with the immunoadsorbent.

For example, in the case of recombinant vaccinia viruses expressing pseudorabies glycoproteins, these viruses can be used to infect experimental animals to raise monoclonal antibodies and/or polyclonal antisera which recognize one or more of these glycoproteins. These monoclonal and/or polyclonal antibodies can then be used as capture antibody in an immunoassay for the detection of PRV-specific antigens in the urine, blood, or feces of a host animal.

Alternatively, pseudorabies glycoproteins can be isolated in crude or pure form from cells infected in vitro with recombinant vaccinia viruses expressing one or more of these glycoproteins. These glycoproteins can then be used in an immunoassay to detect the presence of anti-PRV antibodies in the bodily fluid of host animals as described above.

The invention is illustrated further by the following Examples:

EXAMPLES

Materials and Methods

E. coli Strains

E. coli strains JM101 (Messing et al., 1981. Nucl. Acids Res. 9, 309), MC1060 and MC1061 (Casadaban & Cohen, 1980. J. Mol. Biol. 138, 179), HB101 (Boyer and Rouland-Dussoix, 1969. J. Mol. Biol. 41, 59; Bolivar and Backman, 1979. Methods Enzymol. 8, 245) and $RR_1$ (Bolivar et al., 1977. Gene 2, 95; Peacock et al., 1981. Biochim. Biophys. Acta 655, 243) were used.

Restriction Enzyme Digestion

Enzymes were obtained from New England BioLabs or Boehringer-Mannheim. Digests were performed as described (Maniatis, T., Fritsch, E. F. and Sambrook, J., 1982, Molecular Cloning: A Laboratory Manual. Cold Spring Harbor Laboratory, Cold Spring Harbor, N.Y., pp 104-105.). Digests were incubated at 37° for 1 hr unless otherwise specified.

Treatment of DNA with Calf Intestinal Phosphatase

DNA was dephosphorylated in 50mM Tris-HCl, pH9.0, 1.0mM $MgCl_2$, 0.1 mM $ZnCl_2$ and 1 mM spermidine with 1 ul of calf intestinal phosphatase (Boehringer-Mannheim, 23 units/ul) at 37° for 30 min, sometimes followed by a second 30 min incubation with another 1 ul of enzyme.

Treatment of DNA with DNA Polymerase, Large Fragment (Klenow)

Klenow enzyme was obtained from New England BioLabs and used as described (Maniatis, T., Fritsch, E. F. and Sambrook, J., 1982. Molecular Cloning: A Laboratory Manual. Cold Spring Harbor Laboratory, Cold Spring Harbor, N.Y., pp 112-113).

Treatment of DNA with Mung Bean Nuclease

Mung bean nuclease digestion was performed in 30 mM sodium acetate, pH4.6, 50 mM NaCl, 1 mM $ZnCl_2$, 1 unit mung bean nuclease (Pharmacia), at 37° C. for 10 minutes.

Treatment of DNA with T4 DNA Polymerase

T4 DNA polymerase was obtained from New England BioLabs and used as described (Maniatis, T. Fritsch, E. F. and Sanbrook, J., 1982. Molecular Cloning. A Laboratory Manual. Cold Spring Harbor Laboratory, Cold Spring Harbor, N.Y., p395).

Gel-Purification of Restriction Fragments

DNA was fractionated by size on low-melt agarose (ranging from 0.7% to 3%) gels run in 40 mM Tris-acetate, pH8.0, 2 mM EDTA. The DNA fragment of interest was excised from gel, liquified at 70° C. and diluted in 200 mM NaCl, 50 mM Tris, pH7.5, mM EDTA. The DNA was extracted with phenol, then phenol: chloroform (1:1), followed by ethanol precipitation.

Ligation of DNA Fragments

T4 DNA Ligase was obtained from Boehringer Mannheim. Ligations were performed in 50 mM Tris, pH7.4, 10 mM $MgCl_2$, 10 mM dithiothreitol, 1 mM spermidine, 1 mM adenosine 5'-triphosphate, 0.1 mg/ml bovine serum albumin, 1u T4 DNA ligase, at 15° C. for 30 min. to 3 days unless otherwise specified.

Phosphorylation of Linkers and Ligation to DNA

Linkers and T4 polynucleotide kinase were obtained from New England BioLabs. Linkers were phosphorylated and ligated as described (Maniatis, T., Fritsch, E. F. and Sambrook, J., 1982. Molecular Cloning: A Laboratory Manual. Cold Spring Harbor Laboratory, Cold Spring Harbor, N.Y., pp 396-397).

E coli Transformation

E. coli cells were made competent and transformed with DNA as described (Maniatis T., Fritsch, E. F. and Sambrook, J., 1982. Molecular Cloning: A Laboratory Manual. Cold Spring Harbor, N.Y., pp 250-251).

Isolation and Purification of Plasmid DNA

Preparation of plasmid DNA and purification by cesium chloride-ethidium bromide gradient centrifugation were performed as described (Maniatis, T., Fritsch, E. F. and Sambrook, J., 1982. Molecular Cloning: A Laboratory Manual. Cold Spring Harbor Laboratory, Cold Spring Harbor, N.Y., pp. 90, 91, 93, 94).

Virus and Cells

CV-1 cells, which are kidney cells derived from the African Green Monkey, were obtained from the American Type Culture Collection (ATCC #CCL70) and grown in Minimal Essential Media (MEM; Gibco) supplemented with 10% fetal calf serum (FCS) Hyclone Laboratories, Inc.).

Vaccinia virus strain New York City Board of Health (NYCBH) was obtained from the ATCC (ATCC# VR-325). The virus stock received from ATCC was grown on CV-1 cells in MEM-2% FCS, and this virus was further amplified in spinner cultures of HeLa-S3 cells (ATCC #CCL2.2) for purification on sucrose gradients prior to use for infection in in vivo recombination (IVR) experiments.

Infection and Transfection

CV-1 cells were plated 24 hr before an IVR at $10^6$ cells per 6 cm plate. These cells were infected with vaccinia virus at a multiplicity of infection (MOI) of 1 or 2 in a total volume of 200 ul of MEM-2% FCS. Virus was adsorbed for 40 min at 37° C.; during this time the plates were rocked every 10-15 min to distribute the virus and to keep the plates from drying out. After virus adsorption, 3.3 ml of MEM-2% FCS was added to the cells.

Solution A (250 mM $CaCl_2$, 25 mM HEPES, pH7.12) was added to 20 ug of CsCl gradient-purified DNA (total volume of 30 ul or less) for a final total volume of 250 ul. While air was then bubbled through this solution, 250 ul of solution B (280 mM NaCl, 1.5 mM $Na_2HPO_4$, 25 mM HEPES, pH7.12) was added dropwise, wise, and the solution was incubated at room temperature for 40 min. This solution was then added dropwise to infected cells while the plate was gently swirled.

The infected cells, which had been transfected with DNA right after completion of virus adsorption, were incubated at 37° C. until all the cells were observed to be infected; typically cytopathic effects were seen by 16-20 hr. Virus from the IVR was harvested by freezing and thawing the plates three times. Cells were scraped off the plate into the medium, cell debris was removed by centrifugation in a clinical microfuge for 5 minutes, and the supernatant containing the virus was sonicated for 40 sec and stored at −80° C.

Plaque Purification of Recombinant Virus

The progeny virus was then titered on a monolayer of CV-1 cells on a 6 cm plate. Because the DNA used in the transfection step contained the lacZ gene under the regulation of a vaccinia promoter as well as a gene of interest, i.e. gene encoding antigen, one could detect recombinant virus as blue plaques in the presence of Bluo-Gal (Bethesda Research Laboratories). Because in vivo recombination occurs at a low frequency, the number of progeny from each IVR was determined by a titration, in which the progeny virus was diluted $10^{-1}$ through $10^{-4}$ in MEM-2% FCS. A 6 cm plate of confluent CV-1 cells (passaged 24 hr earlier) was infected with 0.5 ml of diluted virus which was adsorbed for 30 min at 37° C. The medium was then removed by aspiration and the cells were overlaid with 3 ml of DME minus Phenol Red (Gibco)—0.6% agarose (Bio-Rad)—10% FCS—0.1 ug/ml fungizone. This overlay was made by mixing equal volumes of 2×(DME minus Phenol Red-FCS-fungizone) with 1.2% agarose. On day 3, another 3 ml of overlay containing the previous mixture and 400 ug/ml Bluo-Gal (from a freshly prepared stock at 20 mg/ml in dimethyl sulfoxide (DMSO)) was placed over the first agarose overlay. The plates were then screened daily for the number of blue and white plaques; blue plaques first appeared anywhere from 4-48 hr. Plaques were counted and the PFU (plaque-forming units)/ml of progeny virus in the IVR were calculated.

Fifteen to twenty 6 cm plates of CV-1 cells were then infected with approximately 250-300 PFU/plate of the progeny virus. The infection, the first and second agarose overlays and screening of the plaques were all done as described in the previous paragraph. Recombinant (blue) plaques were picked and placed into 2.0 ml MEM-2% FCS and sonicated for 40 sec. A second round of plaque purification was done by infecting cells with 20 ul to 200 ul of this sonicated virus, and this was followed by a third and fourth round of plaque purification.

Virus Amplification

After plaque purification, the resulting virus was amplified on a 6 cm plate of CV-1 cells. This virus was harvested in a total volume of 5 ml and the cells lysed by 3 cycles of freeze-thawing. Cellular debris was removed by centrifugation and the resulting virus was again amplified first on another 6 cm plate of CV-1 cells, and then again on a 15 cm plate of CV-1 cells. The virus particles (in 20 ml) were then concentrated by layering over a 15 ml cushion of 36% (w/v) sucrose in 1 mM Tris-HCl, pH9.0 and centrifuging in the SW28 rotor at 20,000 rpm at 4° C. for 60 min. The virus pellet was resuspended in a small volume of 1 mM Tris-HCl, pH9.0. The concentration of PFU was determined as previously described; in this case the dilutions ranged from $10^{-3}$ to $10^{-8}$.

The virus resulting from the infection of the 15 cm plate of CV-1 cells was trypsinized, then used to infect approximately 1 liter of HeLa-S3 cells in a spinner at an MOI of 1. Virus was trypsinized with an equal volume of 0.25% tryspin (Gibco) for 30 min at 37° C. in a shaker. HeLa-S3 cells were spun down, resuspended in 20 ml DPBS and counted; the cells were then further concentrated by centrifugation and resuspended in a small volume (approximately 2 ml) of DPBS-1% FCS. The appropriate amount of trypsinized virus was added to the cells and adsorbed for 45 min in a shaker at 37° C. The infected cells were then diluted with fresh DME-10% FCS to a final concentration of approximately $4 \times 10^5$ cells/ml. After a 3 day incubation at 37° C., the cells were pelleted, resuspended in approximately 100 ml of 1 mM Tris-HCl, pH9.0, and left on ice for 30 min. The cells were then homogenized in 25 ml aliquots with 10 strokes each in a Dounce homogenizer. The cells were pelleted at 6,000 rpm in the Sorvall SA-600 rotor for 5 min and the supernatant containing the virus was set aside. The pelleted cells were resuspended in 20 ml of 1 mM Tris-HCl, pH9.0, and homogenized again with five strokes of a Dounce homogenizer. The cells were pelleted at 8,000 rpm in the Sorvall SA-600 rotor and the supernatant containing the virus was pooled with the first supernatant. At this point, the virus was frozen at −80C. until further purification through a sucrose cushion and a sucrose gradient. Virus was purified by pelleting through a 15 ml cushion of 36% (w/v) sucrose in 1 mM Tris-HCl, pH9.0, at 20,000 rpm at 4° C. for 60 min in the SW28 rotor. The virus pellet was resuspended in a small volume of 1 mM Tris-HCl, pH9.0, and banded on a 25-40% (w/v) sucrose gradient in 1 mM Tris-HCl, pH9.0, in an SW28 rotor at 15,000 rpm at 4° C. for 40 min. The virus band was collected and repelleted at 20,000 rpm in the SW28 rotor for 60 min at 4° C. The pellet was resuspended in 1 mM Tris-HCl, pH9.0.

Black Plaque Assay

CV-1 cells were plated one day prior to infection at $7 \times 10^5$ cells per 6 cm dish, in MEM containing antibiotics and antimycotics (Sigma) and 10% FCS. Twenty-four hrs later the cells became confluent ($1 \times 10^6$ cells per dish). Growth medium was removed from the cells and replaced with 0.5 ml of medium containing recombinant vaccinia virus vAbT54R or vAbT67 or control virus (NYCBH). Virus was adsorbed to the cells for 30 minutes at 37° C., then the medium was removed by aspiration and the cells were overlaid with 0.6% agarose in DME containing 10% FCS and 0.1 ug/ml fungizone. The cells were then incubated for two days to allow plaques to form.

After the two day incubation, the agarose overlay was removed, leaving the cell monolayer intact on the dish. The cells were washed three times with 3 ml of Dulbecco's phosphate-buffered saline (DPBS: 137 mM NaCl, 2.7 mM KCl, 1.5 mM KH 8.1 mM Na$_2$HPO$_4$, 4.9 mM MgCl$_2$, 9.1 mM CaCl$_2$, pH7.4), and were fixed for 15 min at room temperature, using 3% formaldehyde (Mallinckrodt) in phosphate-buffered saline (PBS: 137 mM NaCl, 2.7 mM KCl, 1.5 mM KH$_2$PO$_4$, 8.1 mM Na$_2$HPO$_4$). The monolayer was washed again three times with 3 ml of DPBS, and was then incubated with primary antibody.

Hybridomas which recognize the glycoprotein gIII of pseudorabies virus (H. Hampl, et al., 1984. J. Virology 52, 583) were obtained from Dr. Tamar Ben-Porat (Vanderbilt University, Nashville, Tenn.), and were grown in vitro to obtain monoclonal antibody in culture supernatant. The monoclonal antibodies M4, M6 and M7 were used as 1:100 dilutions of culture supernatant in 50% normal goat serum (NGS; Colorado Serum Company) in PBS. Two ml of this solution was added to each plate and incubated for 1 hour at 37° C. A monoclonal antibody MCA50 which recognizes the pseudorabies glycoprotein gp50 (Wathen et al., 1985, Virus Research 4, 19) was obtained from Dr. P. A. O'Berry (National Animal Disease Center, USDA, Ames, Iowa). The monoclonal was obtained as ascites fluid. This antibody was diluted 1:500 in 50% NGS, and 2 ml was added to each plate and incubated for 1 hr at 37° C. After the incubation, the antibody solution was removed by aspiration and the monolayer was washed three times with 3 ml of washing buffer (20 mM Tris-HCl, pH7.5, 1M NaCl, 0.05% Tween-20). The cells were then incubated with the secondary antibody, alkaline phosphatase-conjugated goat anti-mouse IgG (heavy and light chain specific; Kirkegaard & Perry Laboratories). This antibody was diluted 1:200 in 10% NGS, and 1 ml was incubated with the monolayer for 1 hr at 37° C. The solution was then removed by aspiration, and the cells were washed three times with 3 ml of washing buffer, and once with Tris-buffered saline (20 mM Tris-HCl, pH7.5, 0.15 M NaCl). Color was developed on plaques which were expressing the antigen of interest by incubating with a precipitating substrate system, BCIP/NBT (5-bromo-4-chloro-3-indolyl-phosphate and nitroblue tetrazolium (Kirkegaard & Perry Laboratories)). The reagent was made up as per manufacturer's instructions, and 2 ml was incubated with the monolayer at room temperature until color developed on the plaques (approximately 30 minutes).

Black Plaque Assay with Immune Serum

Female Balb/c mice, (eight weeks old), were immunized with various doses of vaccinia virus recombinants intraperitoneally. Serum samples were taken on day 21 from three mice immunized with $1 \times 10^7$ pfu of vAbT54R or with $1 \times 10^8$ pfu of vAbT53 (an unrelated recombinant). Serum was obtained on day 14 from three mice immunized with vAbT67. Serum from each group of mice was pooled and used for the black plaque assay to detect the presence of specific antibody.

PK-15 (pig kidney) cells, obtained from L. Enquist, Dupont Co., were grown in DME 10% FCS and plated on 6 cm dishes at $8 \times 10^5$ cells/dish one day prior to infection. The cells were infected with 0.5 ml of PrV at $1.5 \times 10^2$ pfu/ml. The virus was adsorbed to the cells for 30 min at 37° C., then the medium was removed by aspiration and the cells were overlaid with 0.6% agarose containing 10% FCS and 0.1 mg/ml fungizone in DME. The cells were incubated for two days to allow plaques to form.

After the two day incubation, the agarose overlay was removed, leaving the cell monolayer intact on the dish. The cells were washed three times with 3 ml of DPBS, and were fixed for 15 minutes at room temperature, using 3% formaldehyde (Mallinckrodt) in phosphate-buffered saline. The monolayer was washed again three times with 3 ml of DPBS, and was then incubated with primary antibody.

Serum from the recombinant vaccinia-immunized mice was diluted 1:10, 1:25, 1:50, and 1:1000 in 50% NGS (normal goat serum; Colorado Serum Company) in PBS, and 0.5 ml of this solution was incubated with the monolayer for one hour at 37° C. After the incubation, the antibody solution was removed by aspiration and the monolayer was washed three times with 3 ml of washing buffer (20 mM Tris-HCl, pH7.5, 1M NaCl, 0.05% Tween-20). The cells were then incubated with the secondary antibody, alkaline phosphatase-conjugated goat anti-mouse IgG (heavy and light chain specific; Kirkegaard & Perry Laboratories). This antibody was diluted 1:200 in 10% NGS, and 1 ml was incubated with the monolayer for one hour at 37° C. The solution was aspirated after the incubation, and the cells were washed three times with 3 ml of washing buffer, and once with Tris-buffered saline (20 mM Tris, pH7, 5, 0.15 M NaCl). Color was developed on PrV plaques to which specific antibody was bound by incubating with a precipitating substrate system, BCIP/NBT (5-bromo-4-chloro-3-indolyl-phosphate and nitroblue tetrazolium) (Kirkegaard & Perry Laboratories). The reagent was made up as per manufacturer's instruction, and 2 ml was incubated with the monolayer at room temperature until color developed on the plaques (approximately 5 minutes).

Enzyme-Linked Immunosorbant Assay (ELISA)

CV-1 cells were grown to confluence and infected at an MOI of 2 as described in the previous section, except that 0.5 ml of medium containing virus was left on the cells after the 30 minute incubation, and 4.5 ml of fresh medium was added. The cells were then incubated for 18 hours at 37° C.

Following the incubation period, the medium was aspirated from the cell monolayer, and the cells were gently scraped off the dish into 1 ml of DPBS. This mixture was freeze-thawed ($-80°$ C. to 37° C.) three times, and then sonicated. The treated cell pellets were used to coat microtiter plates to supply antigen on a solid phase for ELISA.

Immulon II Removawell strips (Dynatech) were coated in duplicate with 200 ul of the cell pellet for 18 hr at room temperature. The solution was then removed by aspiration, and 200 ul of primary antibody (either M4, M6 or M7 in culture supernatant, used undiluted, or MCA50 in ascites fluid, diluted 1:500 in 50% NGS) was added. The primary antibody was incubated for 6 hrs at 37° C. This solution was removed by aspiration and the wells were washed three times with 0.5 ml of washing buffer (0.05% Tween-20 in PBS, pH7.5). The secondary antibody was a horseradish peroxidase-conjugated goat anti-mouse IgG (heavy and light chain specific; Jackson Immunoresearch) diluted 1:2500 in 10% NGS. It was incubated at 200 ul per well for 1 hr at 37° C. Following the incubation, the solution was removed by aspiration and the wells were washed three times, as described above. Color was developed using 3,3', 5,5'-tetramethyl-benzidine (TMB, Sigma) as the chromagen. Ten mg of TMB were dissolved in 1 ml of DMSO, and 100 ul of this solution as added to 5 ml of acetate/citrate buffer (0.1M sodium acetate, adjusted to pH6.0 with 0.1M citric acid) along with 10 ul of 3% $H_2O_2$ (Parke-Davis). 200 ul of this final solution was added to the wells and the plate was incubated at room temperature for 5 min. The reaction was stopped by the addition of 200 ul of 2.5N $H_2SO_4$. One half of the solution in each well was removed, and the remaining 200 ul was read at 450 nm on the Dynatech Mini-Reader II plate reader.

Metabolic Labeling

CV-1 grown for 24 hr to a density of $10^6$ cells per 6 cm plate and then infected with vaccinia virus at an MOI of 2 for 30 min at 37° C. Two hr later, the cells were labeled with either [$^3$H]glucosamine or [$^{35}$S]methionine. When [$^{35}$S]methionine was used, the labeling medium consisted of 10 ml of methionine-free DME, 3.5% FCS, 2 mM L-glutamine, 100 uCi [$^{35}$S]methionine (New England Nuclears) and carrier methionine (0.3 mg/100 ml). When cells were labeled with [$^3$H]glucosamine, the DME-3.5% FCS lacked leucine and glucose and was supplemented with 167 uCi [$^3$H]glucosamine (New England Nuclear) and leucine (1.46 mg/100 ml). Cells were harvested after approximately 20 hr, washed twice with PBS and lysed with 0.5 ml of immunoprecipitation buffer (IPB: 10 mM Tris-HCl, pH7.2, 650 mM NaCl, 1% Triton X-100, 1% sodium deoxycholate, 0.1% SDS, 5 mM EDTA, 1 mM phenylmethylsulfonylfluoride (PMSF) and 0.1 mg/ml trypsin inhibitor) for 10 min at room temperature. For subsequent immunoprecipitation steps, 1 mM ATP was also included in the buffer. The lysates were stored at −80° C.

PrV-infected BHK-21 cells were also metabolically labelled as described above. Cells were grown to 80% confluency in 6 cm plates and were infected with virus at an MOI of 2.

Preparation of Staphylococcus Aureus

Killed and formalin-fixed *S.aureus* (IgSorb) was obtained as a 10% (w/v) suspension from the Enzyme Center (Malden, Mass.). The cells were washed twice with IPB and pelleted by spinning 5 min in a microfuge. The cells were resuspended to a final concentration of 10% or 20% (w/v) in IPB.

Preformed complexes of *S. aureus* and IgG were prepared by incubating 5 volumes of 10% (w/v) *S. aureus* with 1 volume of anti-vaccinia virus serum for 10 min at 0° C. The complexes were pelleted, washed twice, and resuspended to a final concentration of 20% (w/v) in IPB.

Immunoprecipitation

Immunoprecipitations were carried out on cell lysate samples each labelled with 10 uCi [$^{35}$S]methionine in 0.2 ml of IPB or 10 uCi [$^3$H]glucosamine in 0.4 ml of IPB. All incubations with antibodies or *S.aureus* were done with rocking at 4° C. Each sample was precleared by incubating with 50 ul of preformed immune complex (*S.aureus*-IgG, 20% [w/v]) for 1 hr and then clarifying by centrifugation in the microfuge for 5 min. The supernatant was transferred to a new test tube, and the preclearing was repeated at least once. The resulting supernatant was then treated for another 30 min with 50 ul of 20% (w/v) *S.aureus*. Finally, the supernatant was transferred to a new test tube and incubated with primary antibodies at an appropriate dilution. The next day, 50 ul of 10% (w/v) *S.aureus* were added to the sample, and the incubation was continued 30 min. The *S.aureus* complexes were pelleted by centrifugation and washed with 200 ul of IPB. The suspension was layered over a differential sucrose gradient (400 ul of 10% (w/v) sucrose/0.5M NaCl/IPB, plus 800 ul of 30% (w/v) sucrose/0.14M NaCl/IPB) and spun for 10 min in the microfuge. The resulting precipitate was washed with 200 ul of IPB and resuspended with 20 ul of SDS gel sample buffer (Laemmli, 1970. Nature 227, 680). The sample was boiled for 5 min, centrifuged to remove the precipitate, and removed with a syringe for application on an SDS gel (Laemmli, 1970. Nature 227, 680) which contained an 8% separation gel and a 3% stacking gel. The SDS-polyacrylamide gel electrophoresis was carried out under reducing conditions and was followed by autoradiography of the gel.

PrV Tissue Culture

PrV (pseudorabies virus, Aujeszky's strain) and BHK-21 cells were obtained originally from the American Type Culture Collection (ATCC # VR135 and CCL10, respectively). The cells were grown in DME/10% calf serum (CS) and were passaged biweekly, after trysinization, at a density of $1 \times 10^5$ cells per 10 cm plate. Confluent cells ($1.5-2.0 \times 10^7$ cells) in a 15 cm plate were infected at an MOI of 1 by adding virus in 5 ml of DME/2% CS. The virus was adsorbed for 30 min at 37° C., and 15 ml of DME/2% CS was added. About 24 to 30 hours later, when cytopathic effects were observed in all cells, the medium was harvested, clarified of cellular debris, and stored at −80° C.

The virus titers (PFU) were then established. Confluent BHK-21 cells on 6 cm plates were infected with 0.5 ml of virus at an appropriate dilution. After virus was adsorbed at 37° C. for 30 min, the medium was removed and the cells were overlaid with ml DME containing 0.6% agarose, 10% calf serum, and phenol red. Plaques were visible after three days. On the fourth day, the agarose layer was removed, and the plaques were fixed and stained with 0.1% methylene blue in methanol/- H$_2$O (50:50) for 1 hour. The plates were washed twice with methanol/H$_2$O (10:90) and air-dried.

Purification of PrV Virus

PrV was purified from tissue culture to provide standards for various biochemical and immunological procedures. All operations were carried out at 4° C. or 0° C. unless otherwise specified. The frozen culture medium (500 to 1000 ml) from PrV-infected BHK-21 cells was thawed at 37° C. and clarified by centrifugation at 1000g (3000 rpm, Sorvall GS3 rotor) for 10 min. The sample was concentrated (Millipore Minitan System, PTHK plates, 100,000 NMWL) to about 20 ml, then centrifuged at 27,000 g (14,000 rpm, Beckman SW28 rotor) for 30 min to pellet the virus. Pelleted virus was resuspended in 1 to 5 ml of buffer (TNE: 10 mM Tris, pH7.4/100 mM NaCl/1 mM EDTA) supplemented with 1 mM PMSF, sonicated (multiple bursts, 50% duty cycle, Sonicator Ultrasonic Processor Model W-225 [Heat Systems Ultrasonics, Inc.]), then layered onto a linear sucrose gradient, 20 to 60% (w/v), prepared in TNE/1 mM PMSF buffer in Beckman SW28.1 ultracentrifuge tubes. The gradient was spun for 16 hours at 83,000 g (25,000 rpm, Beckman SW28 rotor), yielding an opaque virus band located about two-thirds down the tube. The band was collected, diluted with TNE/1 mM PMSF to fill another SW28.1 tube, and spun for 30 min at 28,000 g (14,500 rpm, Beckman SW28 rotor). The virus pellet was then resuspended with 1 ml of TNE/1 mM PMSF, sonicated to homogeneity, and aliquoted for storage at −80° C. The integrity of the virus preparation was confirmed by tisssue culture assay, SDS-PAGE gel analysis, and an ELISA using swine anti-PRV serum.

Preparation of PrV Nucleocapsids

PrV nucleocapsids were prepared by the following method. The starting material was a purified preparation of PrV stored at −80° C. in TNE buffer containing 1 mM PMSF. 1.2 ml of the virus preparation, which contained approximately 9 mg protein as determined by Lowry assay (Lowry et al, 1951. J. Biol. Chem. 193, 265) was thawed at 45° C. and then made 1% (v/v) in NP-40 by addition of 133 ul a 10% (v/v) NP-40 stock solution. The sample was incubated 20 min at 45° C. with agitation every 5 min. The nucleocapsids were then pelleted by centrifugation for 30 min in a microfuge at 4° C. The pellet was extracted again with a small volume (133 ul) of 1% NP-40/TNE/1 mM PMSF buffer, for 20 min at 45° C., and centrifuged as before.

Preparation of PrV Genomic DNA

The PrV nucleocapsid pellet was resuspended in 1.6 ml of 10 mM Tris-HCl, pH7.5, 1 mM EDTA (TE) on ice. The following were then added: 30 ul of B-mercaptoethanol, 100 ul of proteinase K (10 mg/ml) and 400 ul of 20% (w/v) N-lauroylsarcosinate. The mixture was incubated for 30 min at 4° C. with occasional gentle rocking. Then, 2.8 ml of 54% (w/v) sucrose was added and the mixture was incubated for 2 hr at 55° C. Following this incubation, 0.8 ml of 5M NaCl was added, and the mixture was extracted with phenol, then with phenol/chloroform and finally with chloroform. The mixture was dialyzed against 4 liters of TE for 36 hr at 4° C. The volume of the DNA mixture was now about 15 ml and was concentrated to about 1 ml using Ficol powder. The dialysis was repeated and then the DNA was concentrated to about 400 ul with sec-butanol. The DNA was dialyzed on top of Millipore VS filters (0.025 um) against 10 ml TE and changed every 30 min for 3 hr.

Preparation of PrV RNA

BHK-21 cells were grown in DME/10% calf serum. Six 10 cm plates of confluent cells were infected with PrV at an MOI of 1 as described in PrV Tissue Culture. After 24 hr, the medium was removed by aspiration and the cells were washed twice with PBS. Cells on each plate were lysed with 2 ml of 4M guanidium thiocyanate, 25 mM sodium citrate, pH7.0, 0.5% sarkosyl, 0.1 M B-mercaptoethanol, and the DNA was sheared by repeated passage of the sample through a 23-gauge needle. The lysate from each plate was layered on a 3 ml cushion of 5.7M CsCl in an SW50.1 polyallomer tube and centrifuged at 35,000 rpm for 16 hr. The pellet in each tube was washed with 70% ethanol and then resuspended in 300 ul of TE per tube.

Southern and Northern Analysis

Agarose gel electrophoresis of DNA and RNA, transfer to nitrocellulose and hybridization to probes made radioactive by nick-translation were all performed essentially as described (Maniatis et al, 1982. Molecular Cloning. A Laboratory Manual. Cold Spring Harbor Laboratory, Cold Spring Harbor, N.Y., pp 150–160, 202–203, 382–389).

Preparation of Vaccinia Genomic DNA

CV-1 cells, on two 10 cm plates, were infected with vaccinia strain NYCBH at a MOI of 10 for 16 to 24 hours or until total apparent cytopathic effects were observed. The plates were washed twice with PBS. Cells were scraped and suspended in 0.5 ml of PBS. Plates were washed with another 0.5 ml of PBS. Both cell suspensions were combined in a 15 ml tube and centrifuged for 10 min at 2000 rpm. The pellet was resuspended in 1.8 ml of 10 mM Tris-HCl, pH7.8, 5 mM EDTA, 10 mM KCl (hypotonic solution) and was incubated on ice for 10 min. After the addition of 0.5 ml of B-mercaptoethanol and 0.2 ml of 10% Triton X-100, the suspension was incubated on ice for 10 min with intermittent shaking. Nuclei were pelleted by centrifugation at 2000 rpm for 10 min. The supernatant was transferred to a new tube and 1 ul of B-mercaptoethanol, 200 ug of proteinase K, 40 ul of 5M NaCl and 200 ul of 10% SDS were added. The suspension was incubated at 37° C. for 1 hr, then extracted once with phenol, twice with phenol/chloroform and once with ether. One-tenth volume of 3M sodium acetate and 2 volumes of ethanol were added. The suspension was incubated at −20 C. for 30 min, then centrifuged for 10 min at 4° C. in a microfuge. The DNA pellet was washed with 70% ethanol, blotted dry, and then resuspended in 200 ul of 10 mM Tris, pH7.5, 1 mM EDTA and 5 ul of 10 mg/ml RNase A.

EXAMPLE 1

Construction of a Monovalent IVR Vector Containing the Vaccinia 11K Promoter (FIGS. 1, 2, 3)

pUC8 (Vieira, J. and Messing, J., 1982. Gene 19, 259–268) was partially digested with HaeII, and the 2,358 base pair (bp) fragment was gel-purified and religated to create pAG3 as shown in FIG. 1A.

pAG3 was digested with NdeI and treated with the large fragment of DNA polymerase (Klenow) to blunt the ends of the fragment. The vaccinia HindIII J fragment containing the thymidine kinase (TK) gene (Weir et al., 1982. Proc. Natl. Acad. Sci. USA 79, 1210; Hruby and Ball, 1982. J. Virol. 43, 403; Weir and Moss, 1983. J. Virol. 46, 530) was digested with HindIII and PvuII, producing a 1,800 bp fragment carrying the TK gene which was gel-purified and treated with Klenow to blunt the ends of the fragment. The two fragments described above were ligated to create pAbT400, in E. coli strain MC1060, as shown in FIG. 1B.

pAbT400 was digested with ClaI and EcoRI, then was treated with CIP. The vaccinia HindIII F fragment which contains the 11K gene (Wittek et al., 1984. J. Virol. 49, 371; Bertholet et al., 1985. Proc. Natl. Acad. Sci. USA 82, 2096), was digested with ClaI and EcoRI to produce a 600 bp fragment carrying the 11K promotor. This fragment was gel-purified and ligated the pAbT400 fragment to create pAbT401, in E. coli strain MC1060, as shown in FIG. 1C.

pAbT401 was digested with EcoRI, and the ends of the DNA were modified as follows: EcoRI-digested pAbT401 was incubated with T4 DNA polymerase in the presence of 0.8 mM dCTP for 5 min. Then, dATP and dTTP were added to a final concentration of 0.8 mM each and the reaction was continued for 10 additional minutes. Finally, the reaction was terminated by incubation at 70° C. for 10 min, and the DNA was purified. The purified DNA was then treated with mung bean nuclease, digested with ClaI, and treated with Klenow. The resulting 600 bp fragment carrying 11K promoter sequences was gel-purified. pEMBL19 (Dente et al., 1983. Nucl. Acids Res. 11, 1645) was digested with SalI, treated with Klenow and CIP, and ligated to the 600 bp fragment to created pAbT750, in strain JM101, as shown in FIG. 1D. The combined treatment with T4 DNA polymerase and mung bean nuclease removed 5 bp of the 11K gene, including the translation initiation ATG codon, as well as the EcoRI site; the sequence is shown in FIG. 1E. The modified 11K promoter was designated 11KΔ5.

Plasmids pMC1871 and pSKS107 (Shapira et al., 1983. Gene 25, 71) were obtained from M. Casadaban (The University of Chicago, Chicago, Ill.). These plasmids contain the E. coli lacZ gene flanked by various restriction endonuclease sites.

pMC1871 was digested to completion with SstI (SacI). Approximately 10 ug of this DNA was partially digested with BamHI and the fragments were separated on a preparative agarose gel. A 5,380 bp band was isolated from this gel. This fragment was missing the 5' end of the lacZ gene from the BamHI site to the unique SacI site found within the lacZ gene (FIG. 2A). pSKS107 was digested to completion with SacI and BamHI and the digestion products were separated on an agarose gel, and a 2,040 bp fragment was isolated. This fragment contained the 5' end of the lacZ gene from a BamHI site to the SacI site (FIG. 2A). The 5380 bp and 2040 bp fragments were ligated to create plasmid pMC1871-7, in E. coli strain RRI, as shown in FIG. 2B.

Preparative amounts of pMC1871-7 were digested to completion with BamHI, the digestion products were separated on an agarose gel, and a fragment of approximately 3,100 bp was isolated. This fragment contained the entire coding region of the lacZ gene except for the first five codons, which were deleted in the original pSKS107 construction (a polylinker from a pUC plasmid was inserted in place of these sequences in the original construction). The 5' end of the lacZ gene had the following predicted sequence: GA TCC GTC GAC CTG CAG CCA AGC TTG GCA. The last codon, GCA, coded for alanine which was the sixth amino acid in the native lacZ protein.

Plasmid pRW120 (Panicali et al., 1983. Proc. Natl. Acad. Sci. USA 80, 5364) contained a PstI fragment subcloned from the HindIII F fragment of vaccinia virus (strain WR) DNA; the PstI fragment spanned a unique BamHI site in the HindIII F fragment. The PstI fragment was inserted into the plasmid vector pBR325 (Bolivar et al., 1977. Gene 2,95) from which the vector BamHI site had been removed. The vaccinia BamHI site was adjacent to a vaccinia transcription promoter region, BamF, which had been used to direct the expression of several foreign genes inserted at the BamHI site. These foreign genes were inserted such that their orientations were consistent (in the same relative orientation for transcription) with the vaccinia BamF gene.

A preparative amount of pRW120 was digested to completion with BamHI and then treated with CIP. Appropriate quantities of BamHI-digested pRW120 and the lacZ fragment from pMC1871-7 were ligated to created plasmid pDP502, in E. coli strain RRI, as shown in FIG. 2C.

Figures 3A, 3B:
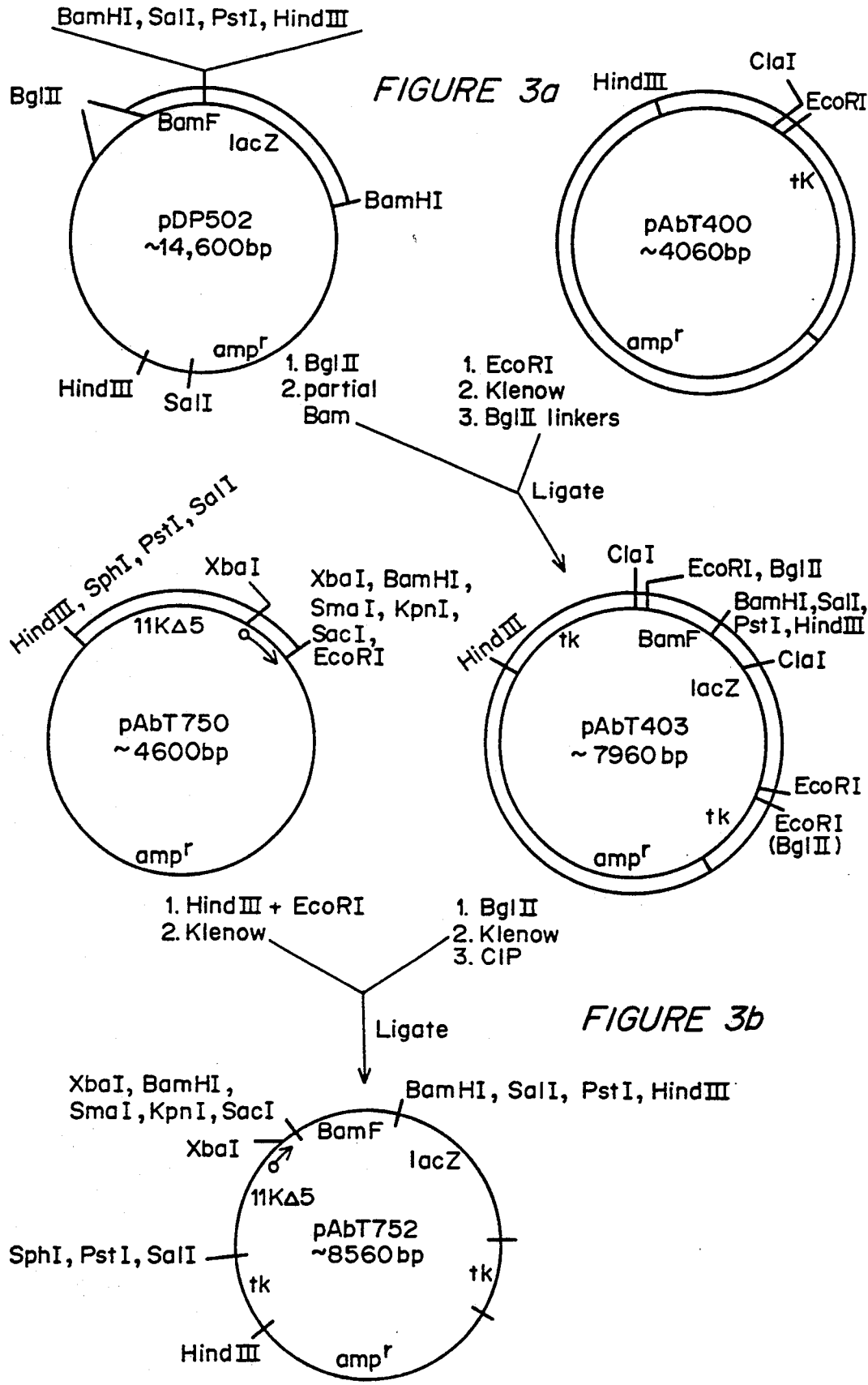

To determine if the coding region of the lacZ gene was in frame with the vaccinia BamF gene at the BamHI site, pDP502 was sequenced through the junction between the 5' end of the lacZ insert and the adjacent vaccinia DNA. This was done using standard dideoxy sequencing techniques (Wallace et al., 1981. Gene 16, 21) directly on pDP502, using a commercially available kit and M13 lacZ sequencing primer (Amersham). The sequence analysis indicated that the lacZ gene was in frame with the ATG of the vaccinia BamF sequence (FIG. 2D), allowing for expression of B-galactosidase.

pDP502 was digested with BglII and then partially digested with BamHI. The resulting 3900 bp fragment containing BamF-lacZ was gel-purified. pAbT400 was digested with EcoRI and treated with Klenow. BglII linkers (d(CAGATCTG); New England BioLabs) were phosphorylated and ligated to the pAbT400 fragment. The resulting 4060 bp fragment was gel-purified and ligated to the 3900 bp BamF-lacZ fragment to create pAbT403, in E.coli strain MC1060, as shown in FIG. 3A.

pAbT403 was digested with BglII and treated with Klenow and CIP. pAbT750 was digested with HindIII and EcoRI and treated with Klenow. The resulting 600 bp fragment containing the modified 11K promoter (11KΔ5) was gel-purified. These two fragments were ligated to create pAbT752, in E. coli strain MC1060, as shown in FIG. 3B.

pAbT752 is a vector for use in in vivo recombination (IVR) experiments in vaccinia. pAbT752 contains the vaccinia TK gene for directing recombination, a lacZ gene under the control of the vaccinia BamF promoter, the 11KΔ5 promoter followed by a multiple cloning site for insertion and expression of foreign antigens containing their own translation initiation ATG codon, and a bacterial replicon and ampicillin-resistance gene for growth and selection in E. coli.

EXAMPLE 2

Construction of a Monovalent IVR Vector Containing the Vaccinia 7.5K Promoter (FIG. 4)

The 7.5K promoter is located on an approximately 1000 bp SalI fragment of vaccinia (Venkatesan et al, 1981. Cell 25, 805). Purified vaccinia DNA was digested with SalI and a mixture of 1000 bp fragments was gel-purified. pEMBL18 (Dente et al, 1983. Nucl. Acids Res. 11, 1645) was digested with SalI, treated with CIP and ligated to the mixture of vaccinia 1000 bp fragments. The plasmid containing the 7.5K promoter was distinguished from plasmids containing the other 1000 bp fragments by the presence of a ScaI restriction site about 270 bp from the end of the 7.5K-containing fragment. This plasmid was designated pAbT4000, as shown in FIG. 4A.

pAbT4000 was digested with HincII and ScaI and the resulting 270 bp fragment containing the 7.5K promoter was gel-purified. pEMBL18 was digested with HincII, treated with CIP and ligated to the 270 bp fragment to create pAbT4001, in E. coli strain JM101, as shown in FIG. 4B.

pAbT752 was digested with SphI and KpnI, treated with CIP, and the resulting 7900 bp fragment was gel-purified. pAbT4001 was digested with SphI and KpnI, and the resulting 300 bp fragment containing the 7.5K promoter was gel-purified. The 7900 bp and 300 bp fragments were ligated to create pAbT4007, in E. coli strain MC1061, as shown in FIG. 4C.

pAbT4007 is a vector for use in in vivo recombination (IVR) experiments in vaccinia. pAbT4007 is identical to pAbT752 as described in Example 1, except that the 7.5K promoter was substituted for

EXAMPLE 3

Figure 7A:
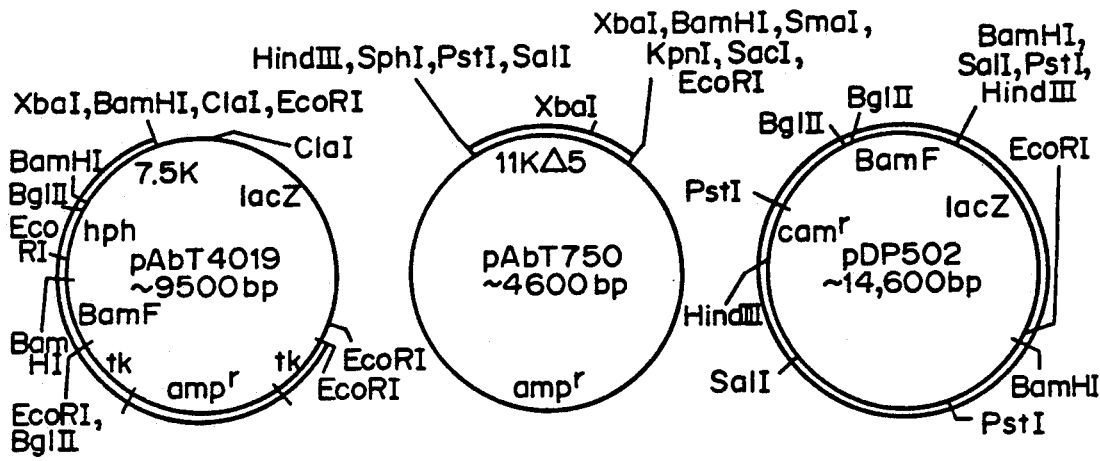
Figure 7B:
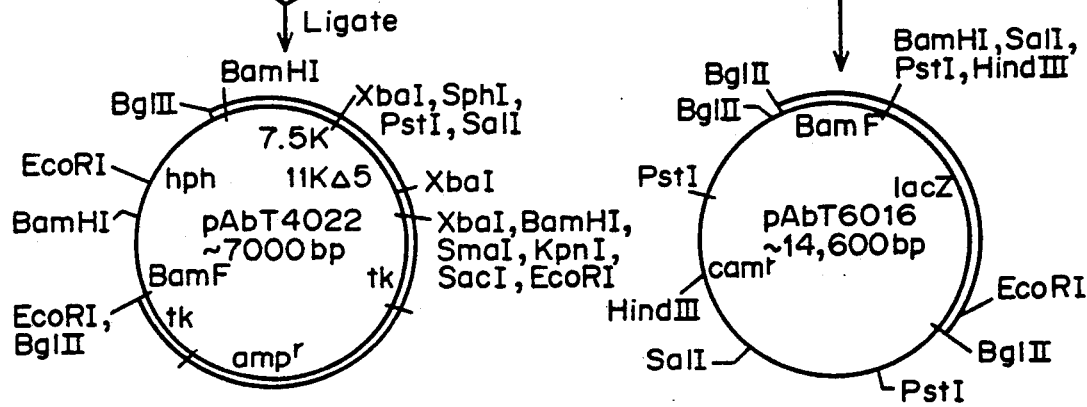
Figure 7C:
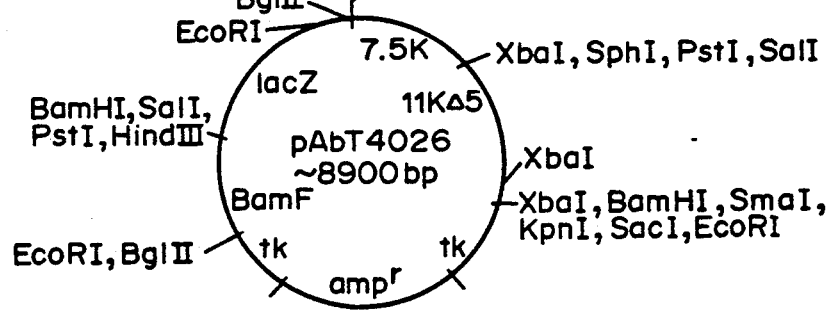

Construction of Divalent IVR Vectors Containing the Vaccinia 7.5K and and 11KΔ5 promoters (FIGS. 5, 6, 7)

pSKS106 (Shapira et al, 1983. Gene 25, 71) was digested with SmaI and treated with CIP. ClaI linkers (d(CATCGATG); New England BioLabs) were phosphorylated and ligated to the pSKS106 fragment. Excess linkers were cleaved with ClaI and the resulting fragment was gel-purified and re-ligated to create pSKS106-C, in E. coli strain MC1060, as shown in FIG. 5A.

pSKS106-C was digested with BamHI and SstI and the resulting 1950 bp fragment containing the 5' end of the lacZ gene was gel-purified. pMC1871 (Shapira et al, 1983. Gene 25, 71) was partially digested with BamHI, then completely digested with SstI, and the resulting 5400 bp fragment lacking the 5' end of the lacZ gene was gel-purified. The two fragments were ligated to create pMC1871-C, as shown in FIG. 5B.

pMC1871-C was digested with BamHI and the resulting 3100 bp fragment containing the lacZ gene was gel-purified. pBR322 (Bolivar et al, 1977. Gene 2, 95) was digested with BamHI, treated with CIP and ligated to the 3100 bp fragment to create pZOB as shown in FIG. 5C.

pZOB was digested with BamHI and the resulting 3100 bp fragment containing lacZ was gel-purified. pAG3 was digested with NdeI and treated with Klenow. BamHI linkers (d(CGGATCCG); New England BioLabs) were phosphorylated and ligated to the pAG3 fragment. Excess BamHI linkers were cleaved with BamHI and the resulting fragment was gel-purified and re-ligated to create pAbT2010. pAbT2010 was digested with BamHI, treated with CIP and ligated to the 3100 bp lacZ fragment to create pAbT2011, as shown in FIG. 5D.

pAbT2011 was digested with BamHI and the resulting 3100 bp fragment containing lacZ was gel-purified. pAbT4001 was digested with BamHI, treated with CIP and ligated to the 3100 bp lacZ fragment to create pAbT4006, as shown in FIG. 5E.

pAbT403 was digested with BamHI and treated with CIP. pLG83 (Gritz and Davies, 1983, Gene 25, 179) was digested with BamHI and the resulting 1300 bp fragment containing hygromycin phosphotransferase (hph) was gel-purified. The two fragments were ligated to create pAbT4009, in *E. coli* strain MC1061, as shown in FIG. 6A.

pAbT4009 was digested with SacI and SalI, treated with CIP and the resulting 7300 bp fragment was gel-purified. pAbT4006 was digested with SacI and SalI and the resulting 2200 bp fragment was gel-purified. The two fragments were ligated to create pAbT4010, in *E. coli* strain MC1061, as shown in FIG. 6B.

pAbT4010 was digested with SalI, treated with Klenow and the resulting 9500 bp fragment was gel-purified and re-ligated to create pAbT4017, in *E. coli* strain MC1061, as shown in FIG. 6C.

pAbT 4017 was partially digested with XbaI and treated with Klenow, and the resulting 9500 bp fragment was gel-purified and re-ligated to create pAbT4019, in *E. coli* strain MC1061, as shown in FIG. 6D.

pAbT4019 was digested with XbaI, treated with Klenow, partially digested with EcoRI and treated with CIP, and the resulting 6500 bp fragment was gel-purified. pAbT750 was digested with HindIII, treated with Klenow and digested with EcoRI, and the resulting 600 bp fragment containing the 11KΔ5 promotor was gel-purified. The two fragments were ligated to create pAbT4022, in *E. coli* strain MC1061, as shown in FIG. 7A.

pDP502 was partially digested with BamHI and the resulting 14,600 bp fragment was gel-purified and treated with Klenow. BglII linkers (nonphosphorylated d(GGAAGATCTTCC); New England BioLabs) were ligated to the DNA which was then gel-purified. The DNA was then heated to 60° C. and allowed to cool slowly before additional ligase was added to close the plasmid, designated pAbT6016, in *E. coli* strain HB101, as shown in FIG. 7B.

pAbT4022 was digested with BglII and treated with CIP and the resulting 5000 bp fragment was gel-purified. pAbT6016 was digested with BglII and the resulting 3900 bp fragment was gel-purified. The two fragments were ligated to create pAbT4026, in *E. coli* strain MC1061, as shown in FIG. 7C.

pAbT4026 is a divalent vector for use in in vivo recombination (IVR) experiments in vaccinia. pAbT4026 contains the same elements for bacterial growth and selection and vaccinia recombination and selection as pAbT752 described in Example 1. pAbT4026 differs from pAbT752 in that pAbT4026 contains two vaccinia promoters, 7.5K and 11KΔ5, each followed by unique multiple cloning sites for insertion and expression of foreign antigens containing their own translation initiation ATG codon.

EXAMPLE 4

Construction of Divalent IVR Vectors Containing the Vaccinia 7.5K and 30K Promoters (FIGS. 8 and 9)

pAG3 was digested with NdeI and treated with Klenow. HindIII linkers (d(CAAGCTTG); New England BioLabs) were phosphorylated and ligated to the pAG3 fragment. Excess linkers were digested with HindIII and the resulting 2260 bp fragment was gel-purified and re-ligated to create pAbT2009, as shown in FIG. 8A.

pAbT2009 was digested with HindIII and treated with CIP. The 30K promoter is located on the 2400 bp HindIII M fragment of vaccinia (Perkus et al., 1985. Science 229, 981). This 2400 bp fragment was ligated to the pAbT2009 fragment to create pAbT3100, as shown in FIG. 8B.

pAbT3100 was digested with SalI and AvaI and the resulting 500 bp fragment was gel-purified. The fragment was partially digested with RsaI and the resulting 420 bp fragment containing the 30K promoter was gel-purified. pEMBL8 (Dente et al., 1983. Nucl. Acids Res. 11, 1645) was digested with SalI and SmaI, treated with CIP and ligated to the 420 bp fragment, containing the 30K promoter, to create pAbT3101, as shown in FIG. 8C.

pAbT3101 was digested with EcoRI and treated with Klenow. BamHI linkers (d(CGGATCCG); New England BioLabs) were phosphorylated and ligated to the fragment, excess linkers were cleaved with BamHI and the resulting 4420 bp fragment was gel-purified and treated with CIP. pAbT2011 was digested with BamHI and the resulting 3100 bp fragment containing BamF-lacZ was gel-purified. The two fragments were ligated to create pAbT3103, as shown in FIG. 8D.

pAbT3103 was digested with SalI and BamHI and the resulting 420 bp fragment containing the 30K promoter was gel-purified. pEMBL18 (Dente et al., 1983. Nucl Acids Res. 11, 1645) was digested with SalI and BamHI, treated with CIP and ligated to the 420 bp 30K promoter fragment to create pAbT4024, in *E. coli* strain pAbT4024 was digested with KpnI and SalI and the resulting 420 bp fragment containing the 30K promoter was gel-purified. pAbT4022 was digested with KpnI and SalI and treated with CIP. The resulting 6500 bp fragment was gel-purified and ligated to the 420 bp 30K promoter fragment to create pAbT4025, in *E. coli* strain MC1061, as shown in FIG. 9A.

pAbT4025 was partially digested with BglII and treated with CIP, and the resulting 4800 bp fragment was gel-purified. pAbT6016 was digested with BglII and the resulting 3900 bp fragment containing BamF-lacZ was gel-purified. The two fragments were ligated to create pAbT4027, in *E. coli* strain MC1061, as shown in FIG. 9B.

pAbT4027 is a divalent vector for use in in vivo recombination (IVR) experiments in vaccinia. pAbT4027 is identical to pAbT4026 except that in pAbT4027 the 30K promoter is substituted for the 11KΔ5 promoter.

EXAMPLE 5

Figure 10A:
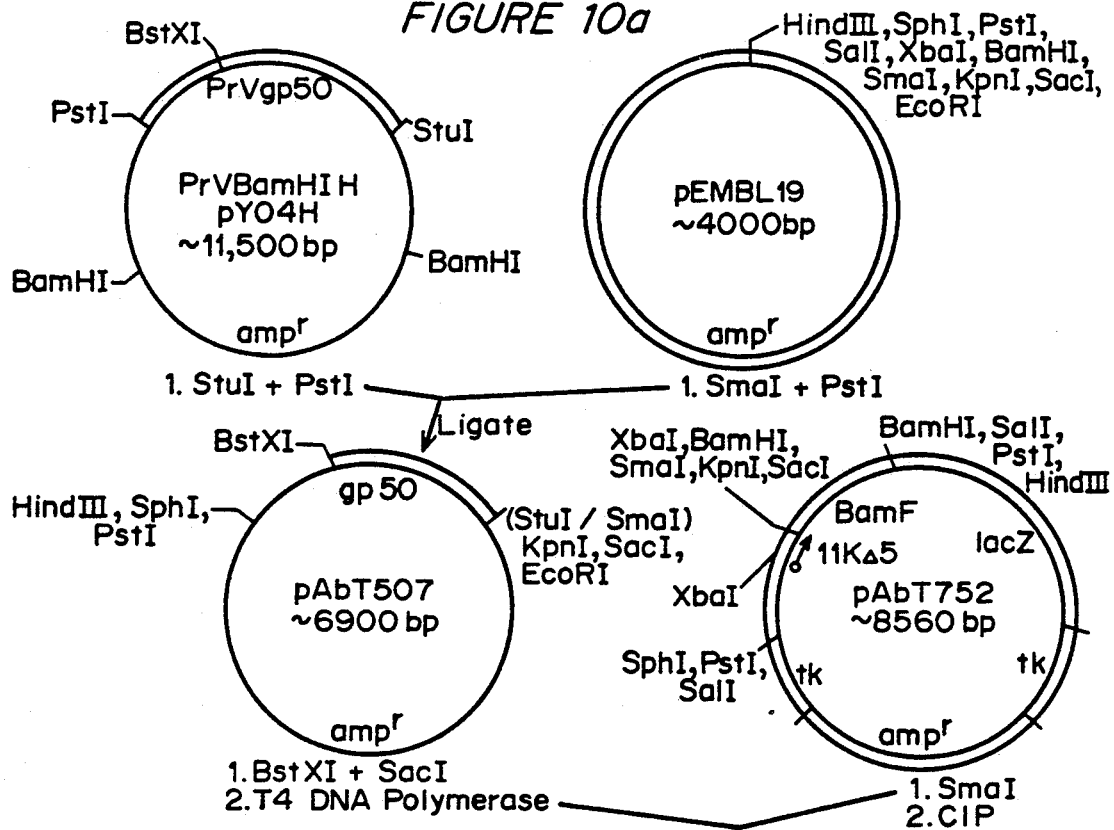
FIGS. 10 A-C show the construction of the IVR vectors pAbT756 and pAbT4018, each containing the pseudorabies gp50 gene. The gp50 gene is under the control of the vaccinia 11KΔ5 promoter in pAbT756 and under the control of the vaccinia 7.5K promoter in pAbT4018.
Figure 10B:
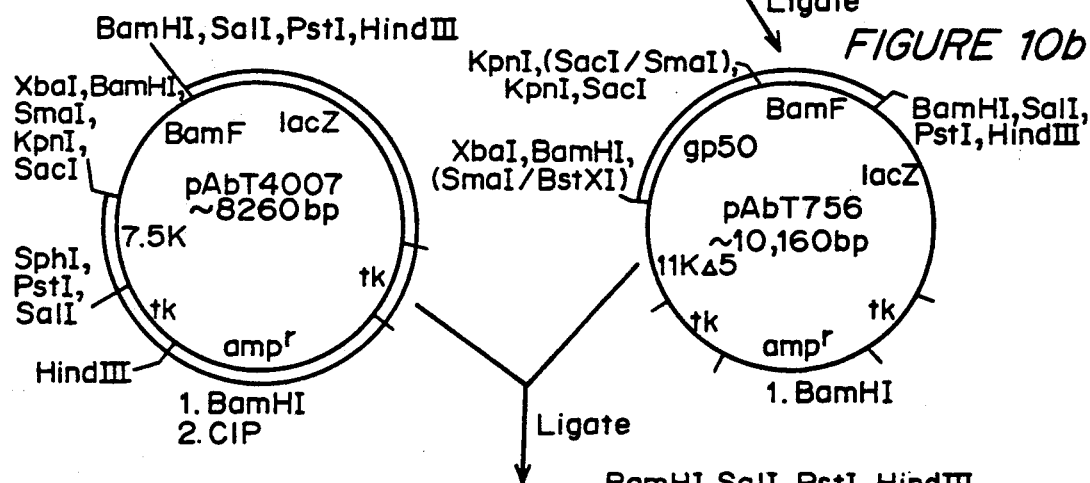
Figure 10C:
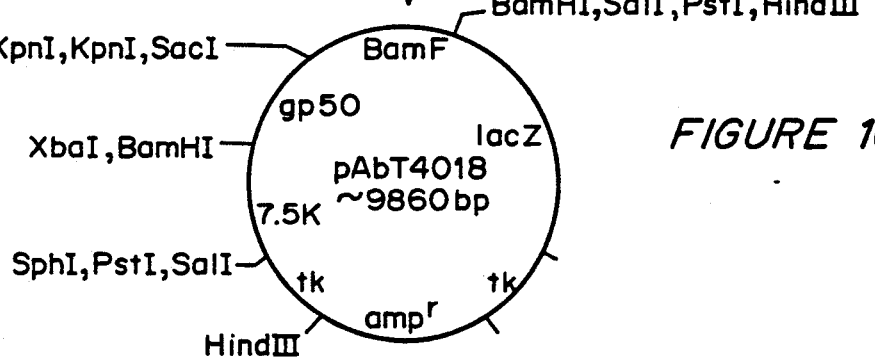
Figure 13A:
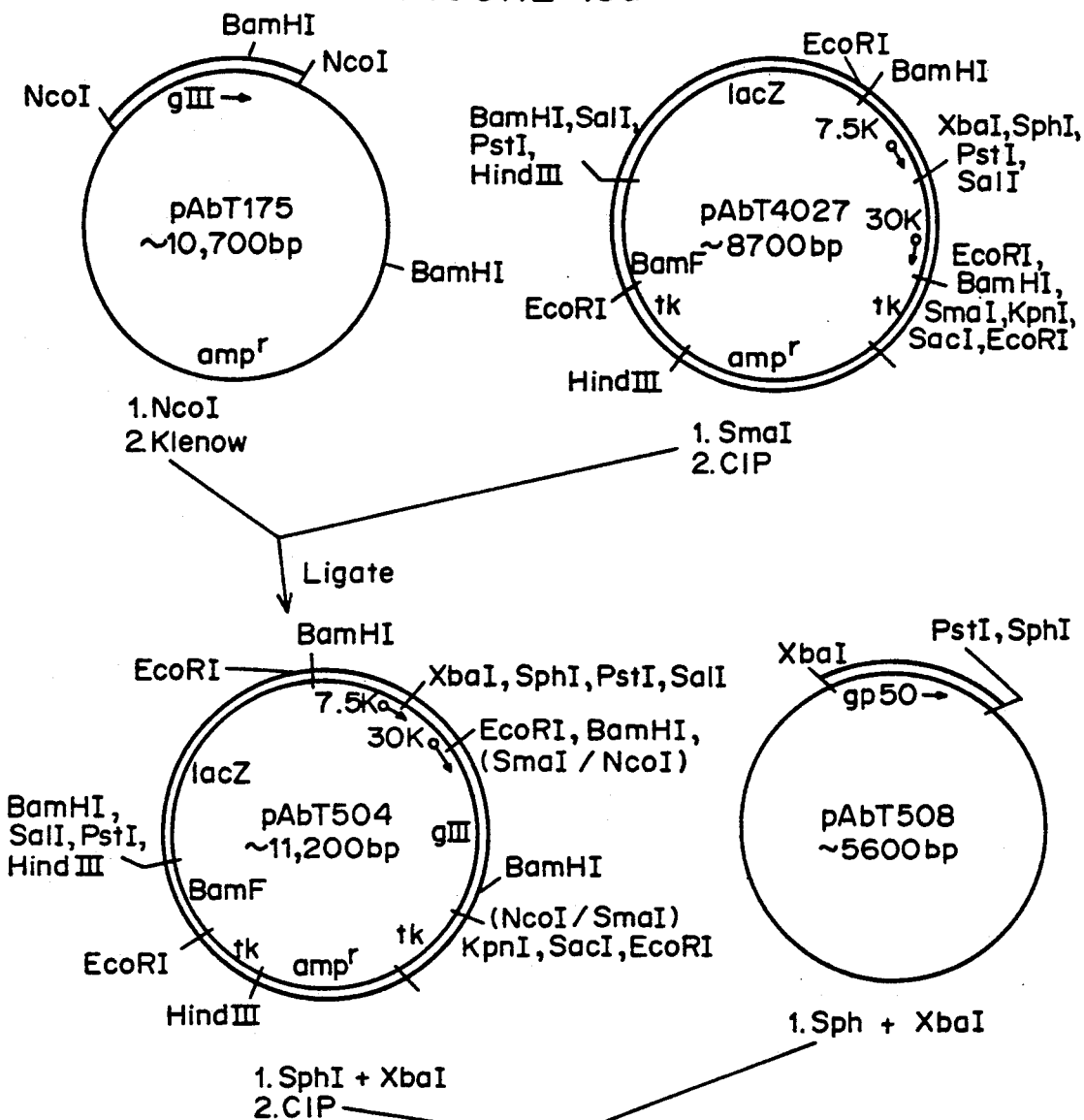
FIGS. 13 A and B show the construction of the divalent IVR vector pAbT503 containing the gp50 gene under the control of the vaccinia 7.5K promoter and the gIII gene under the control of the vaccinia 30K promoter.
Figure 13B:
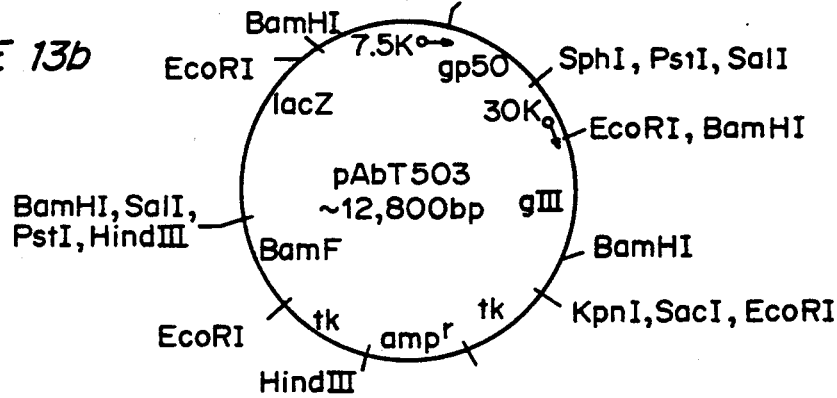
Figures 14A, 14B, 14C:
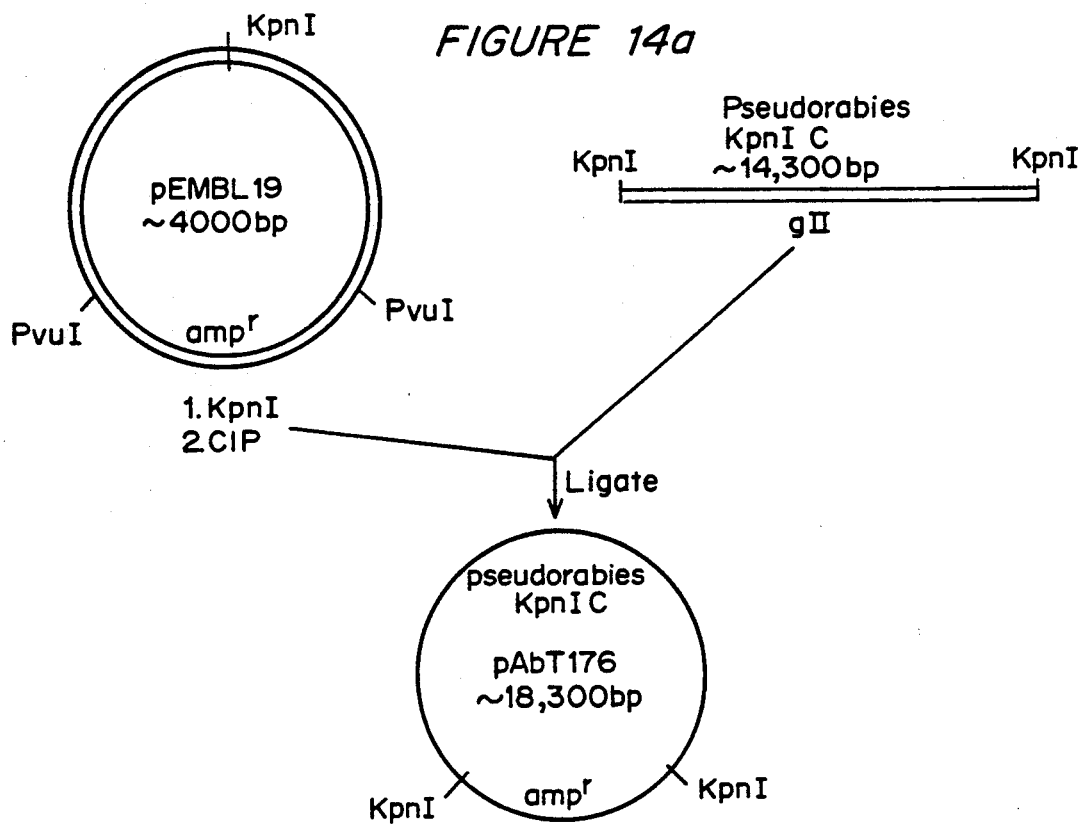
FIG. 14 (parts A-C) shows the construction of plasmid pAbT765 containing the pseudorabies gII gene.
Figure 15A:
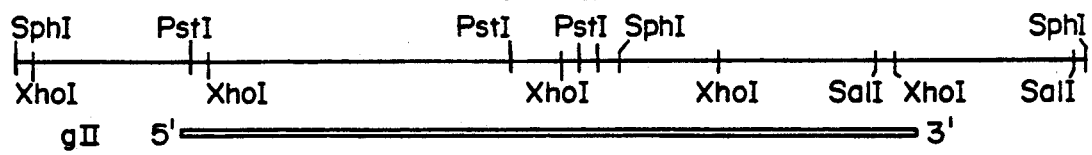
FIGS. 15 and 16 show the construction of pAbT781, an IVR vector containing the pseudorabies gII gene under the control of the vaccinia 7.5K promoter.
Figure 15B:
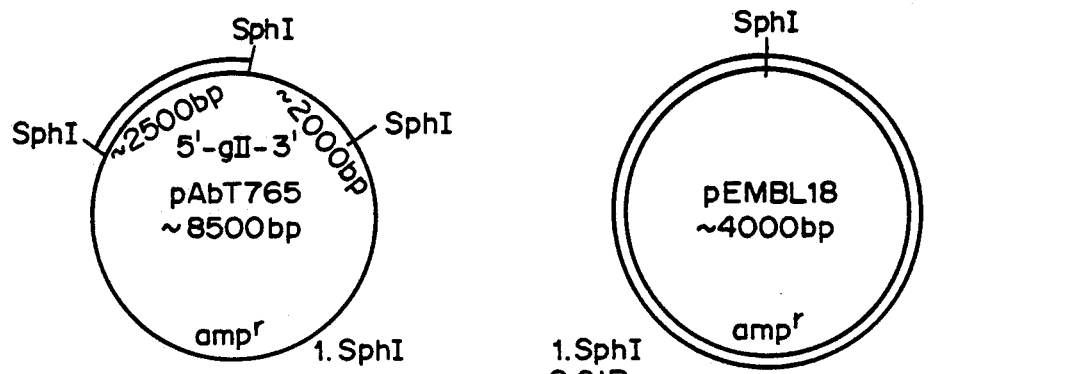
Figure 15C:
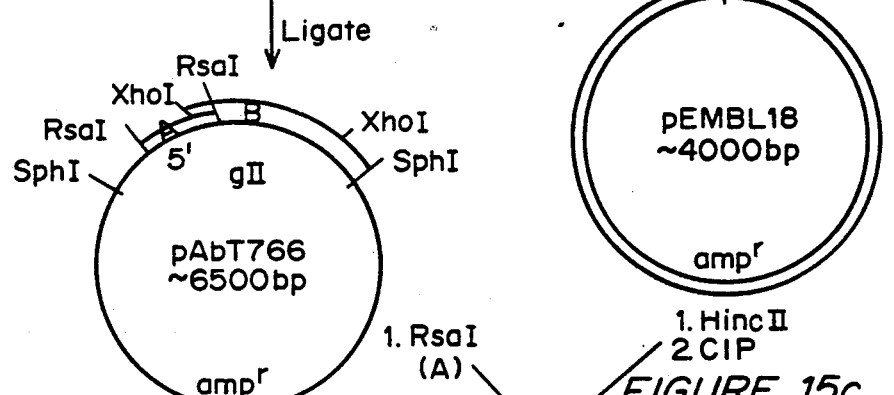
Figure 15D:
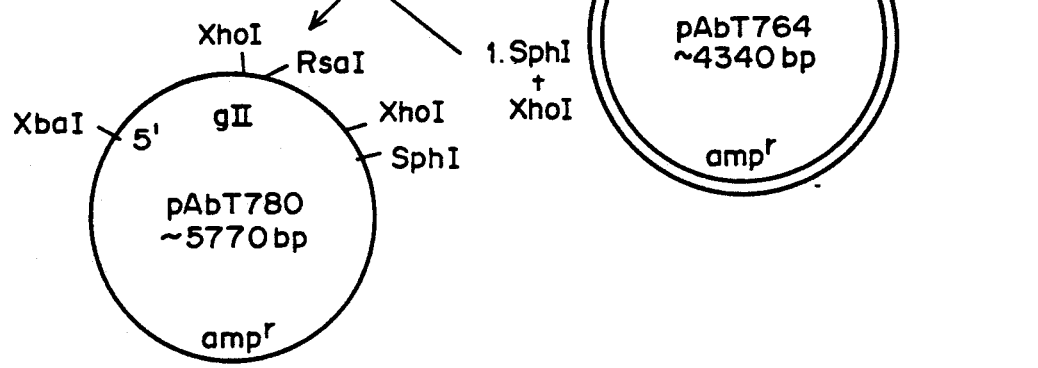

Construction of a Monovalent IVR Vector Containing the Pseudorabies Gene Encoding Glycoprotein gp50 Under the Control of the Vaccinia 11KΔ5 Promoter (FIG. 10)

Pseudorabies (PrV) is a herpesvirus containing several surface glycoproteins (Ben-Porat and Spear, 1970. Virol. 41, 265). The pseudorabies gene encoding glycoprotein gp50 has been localized to the BamHI H fragment of the pseudorabies genome (Wathen and Wathen, 1984. J. Virol. 51, 57).

Figure 16C:
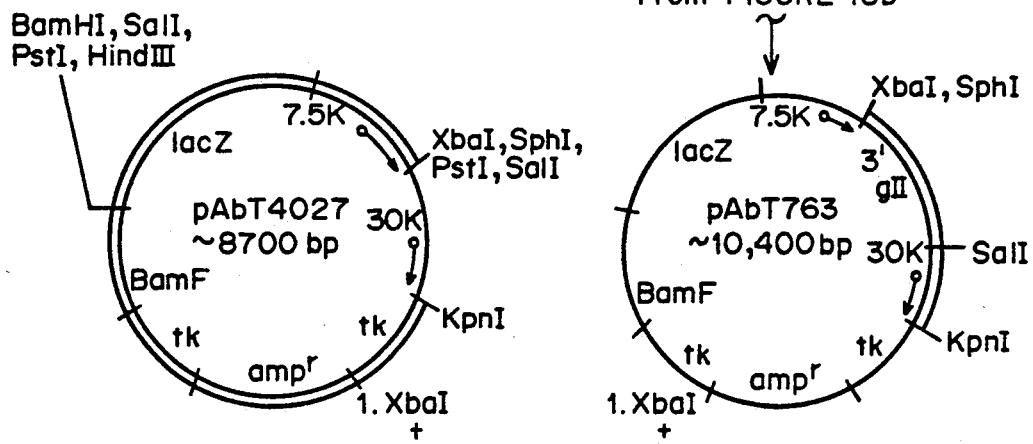
Figure 16D:
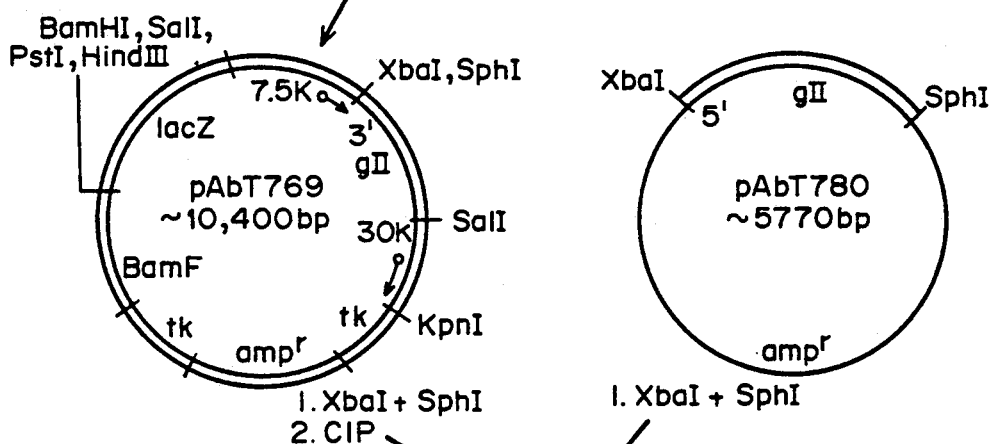
Figure 16E:
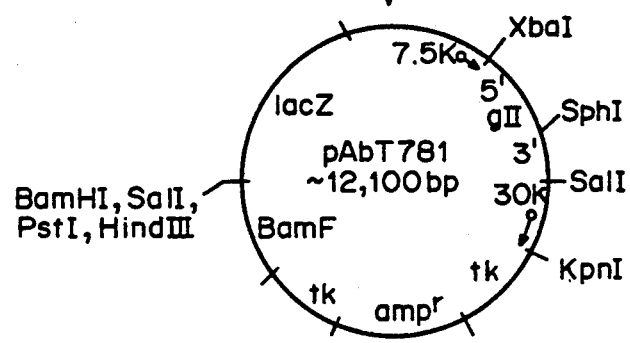

Plasmid pY104H (Wathen and Wathen, 1984. J. Virol. 51, 57) containing the BamHI H fragment cloned into pBR322 (Bolivar et al, 1977. Gene 2, 95) was digested with StuI and PstI, and the resulting 2900 bp fragment containing gp50 was gel-purified. pEMBL19 (Dente et al., 1983. Nucl. Acids Res. 11, 1645) was digested with SmaI and PstI and ligated to the 2900 bp fragment to create pAbT507, as shown in FIG. 10A.

pAbT507 was digested with BstXI and SacI and treated with T4 DNA polymerase, and the resulting 1600 bp fragment containing gp50 was gel-purified. pAbT752 was digested with SmaI, treated with CIP and ligated to the 1600 bp fragment to create pAbT756, as shown in FIG. 10B.

pAbT756 is a vector for insertion and expression of pseudorabies gp50 in vaccinia. pAbT756 contains the pseudorabies gp50 gene under the control of the vaccinia 11KΔ5 promoter, the vaccinia TK gene for directing recombination in vaccinia, a lacZ gene under the control of the BamF promoter for selection of recombinants and a bacterial replicon and ampicillin-resistance gene for growth and selection in *E. coli.*

EXAMPLE 6

Construction of a Monovalent IVR Vector Containing the Pseudorabies Gene Encoding Glycoprotein gp50 Under the Control of the Vaccinia 7.5K Promoter (FIG. 10)

pAbT756 was digested with BamHI and the resulting 2380 bp fragment was gel-purified. pAbT4007 was digested with BamHI and treated with CIP, and the resulting 7480 bp fragment was gel-purified. The two fragments were ligated to create pAbT4018, in *E. coli* strain MC1061, as shown in FIG. 10C.

pAbT4018 is a vector for insertion and expression of pseudorabies gp50 in vaccinia. pAbT4018 is identical to pAbT756 described in Example 5 except that the vaccinia 7.5K promoter is substituted for the 11KΔ5 promoter.

EXAMPLE 7

Construction of a Monovalent IVR Vector Containing the Pseudorabies Gene Encoding Glycoprotein gIII Under the Control of the Vaccinia 11KΔ5 Promoter (FIG. 11)

The pseudorabies gene encoding glycoprotein gIII has been localized to the KpnI A and J fragments of the pseudorabies genome (Robbins et al, 1984. J. Mol. Appl. Genet. 2, 485); these fragments overlap the pseudorabies BamHI B and K fragments. Plasmid pX39B, which contains the pseudorabies BamHI B and K fragments, was obtained from Dr. Michael Wathen (National Animal Disease Center, USDA, Ames, Iowa).

pX39B was digested with BamHI, and the 4300 bp BamHI K fragment, containing the 3′ end of gIII, was gel-purified. pEMBL19 (Dente et al., 1983. Nucl. Acids Res. 11, 1645) was digested with BamHI, treated with CIP and ligated to the 4300 bp fragment to create pAbT191, as shown in FIG. 11A.

pX39B was digested with BamHI and SphI and the 2400 bp fragment containing the 5′ end of gIII was gel-purified. pEMBL18 was digested with BamHI and SphI and ligated to the 2400 bp fragment to create pAbT174, as shown in FIG. 11B.

pAbT191 was digested with BamHI and the 4300 bp fragment was gel-purified. pAbT174 was digested with BamHI, treated with CIP and ligated to the 4300 bp fragment to create pAbT175, as shown in FIG. 11C.

pAbT175 was digested with NcoI, treated with Klenow, and the resulting 2500 bp fragment containing gIII was gel-purified. pAbT752 was digested with SmaI and treated with CIP, and was ligated to the 2500 bp fragment to create pAbT502, as shown in FIG. 11D.

pAbT502 is a vector for insertion and expression of pseudorabies gIII in vaccinia. pAbT502 is identical to pAbT756 described in Example 5 except that pseudorabies gIII is substituted for pseudorabies gp50.

EXAMPLE 8

Construction of a Monovalent IVR Vector Containing the Pseudorabies Gene Encoding Glycoprotein gIII Under the Control of the Vaccinia 7.5K Promoter (FIG. 11)

pAbT175 was digested with NcoI, treated with Klenow, and the resulting 2500 bp fragment containing the gIII gene was gel-purified. pAbT4007 was digested with SmaI, treated with CIP, and was ligated to the 2500 bp fragment to create pAbT501, as shown in FIG. 11E.

pAbT501 is a vector for insertion and expression of pseudorabies gIII in vaccinia. pAbT501 is identical to pAbT502 except that the vaccinia 7.5K promoter is substituted for the 11KΔ5 promoter.

EXAMPLE 9

Construction of a Divalent IVR Vector Containing the Pseudorabies Gene Encoding Glycoprotein gIII Under the Control of the 7.5K Promoter and the Pseudorabies Gene Encoding glycoprotein gp50 Under the Control of the Vaccinia 30K Promoter (FIG. 12)

pY104H (Wathen and Wathen, 1984. J. Virol. 51, 57) was digested with StuI and BstXI and treated with T4 DNA polymerase, and the 1600 bp fragment containing gp50 was gel-purified. pEMBL19 (Dente et al. 1983. Nucl. Acids Res. 11, 1645) was digested with HincII and treated with CIP, and then ligated to the 1600 bp fragment to create pAbT508, as shown in FIG. 12A.

pAbT508 was digested with HindIII and XbaI and treated with Klenow, and the resulting 1600 bp fragment containing gp50 was gel-purified. pAbT4027 was digested with SmaI, treated with CIP, and then ligated to the 1600 bp fragment to create pAbT505, as shown in FIG. 12B.

pAbT175 was digested with NcoI, treated with Klenow and the resulting 2500 bp fragment containing gIII was gel-purified. pAbT505 was digested with XbaI, treated with Klenow and CIP, and was ligated to the 2500 bp fragment to create pAbT506, as shown in FIG. 12C.

pAbT506 is a divalent vector for the insertion and expression of pseudorabies gp50 and gIII in vaccinia. pAbT506 contains the pseudorabies gp50 gene under the control of the vaccinia 30K promoter, the pseudorabies gIII gene under the control of the vaccinia 7.5K promoter, the vaccinia TK gene for directing recombination in vaccinia, a lacZ gene under the control of the vaccinia BamF promoter for selection of recombinants and a bacterial replicon and ampicillin-resistance gene for growth and selection in E. coli.*

EXAMPLE 10

Construction of a Divalent IVR Vector Containing the Pseudorabies Gene Encoding Glycoprotein gp50 Under the Control of the Vaccinia 7.5K Promoter and the Pseudorabies Gene Encoding Glycoprotein gIII Under the Control of the Vaccinia 30K Promoter (FIG. 13)

pAbT175 was digested with NcoI and treated with Klenow and the resulting 2500 bp fragment containing gIII was gel-purified. pAbT4027 was digested with SmaI, treated with CIP, and was ligated to the 2500 bp fragment to create pAbT504, as shown in FIG. 13A.

pAbT508 was digested with SphI and XbaI and the resulting 1600 bp fragment containing gp50 was gel-purified. pAbT504 was digested with SphI and XbaI, treated with CIP and ligated to the 1600 bp fragment to create pAbT503, as shown in FIG. 13B.

pAbT503 is a divalent vector for the insertion and expression of pseudorabies gp50 and gIII in vaccinia. pAbT503 is identical to pAbT506 except that the gp50 gene is under the control of the vaccinia 7.5K promoter and the gIII gene is under the control of the vaccinia 30K promoter.

EXAMPLE 11

Identification and Isolation of the PrV Gene Encoding gII (FIG. 14)

The pseudorabies gII gene was located on the PrV genome by virtue of its homology to Herpes Simplex Virus (HSV) gB (Robbins et al., 1985. 10th International Herpesvirus Workshop, Ann Arbor, Mich.). A 6900 bp BamHI fragment containing HSVgB in pBR322 was obtained from Dr. Lynn Enquist (E. I. duPont de Nemours and Co.; Wilmington, Del.). PrV genomic DNA was digested with KpnI and the resulting fragments were separated on an agarose gel and transferred to nitrocellulose. The filter was then hybridized to HSVgB labeled with $^{32}P$ by nicktranslation. The 14,300 bp KpnI C fragment of PrV contained sequences homologous to the HSVgB probe. About 30 ug of PrV genomic DNA was digested with KpnI and the 14,300 bp KnpI C fragment was gel-purified. pEMBL19 (Dente et al, 1983. Nucl. Acids Res. 11, 1645) was digested with KpnI, treated with CIP and ligated to the KpnI C fragment to create pAbT176, in *E. coli* strain JM101, as shown in FIG. 14A.

pAbT176 was digested with SalI, SphI and PvuI to generate a restriction map of the KpnI C fragment, as shown in FIG. 14B.

pAbT176 was subjected to Southern analysis using various combinations of restriction digests with KpnI, SphI, PvuI and SalI, using a 3200 bp XhoI-BamHI fragment of HSVgB as a probe. Two SphI fragments, of about 2000 bp and 2500 bp, contained sequences homologous to the gB probe.

pAbT176 was partially digested with SphI and the resulting 4500 bp fragment, containing the 2000 bp and 2500 bp SphI fragments, was gel-purified. pEMBL18 (Dente et al, 1983. Nucl. Acids Res. 11, 1645) was digested with SphI, treated with CIP and ligated to the 4500 bp fragment containing gII to create pAbT765, as shown in FIG. 14C.

EXAMPLE 12

Construction of a Monovalent IVR Vector Containing the Pseudorabies Gene Encoding Glycoprotein gII Under the Control of the Vaccinia 7.5K Promoter (FIGS. 15 and 16)

A restriction map of the PrV fragment in pAbT765 was determined by restriction enzyme digestion (FIG. 15A). The nucleotide sequence of the gene encoding gII has been determined (Robbins et al., 1985. Tenth International Herpesvirus Workshop, Ann Arbor, Mich.); the region encoding gII is shown in FIG. 15A.

pAbT765 was digested with SphI and the resulting 2500 bp fragment containing the 5′ end of the gII gene was gel-purified. pEMBL18 (Dente et al., 1983. Nucl. Acids Res. 11, 1645) was digested with SphI, treated with CIP and ligated to the 2500 bp fragment to create pAbT766, as shown in FIG. 15B.

pAbT766 was digested with RsaI and the 335 bp fragment containing the 5′ end of the gII gene, beginning 22 bp upstream (to the 5′ side) from the translation initiation ATG codon and extending through codon 104 of the gII gene, was gel-purified. pEMBL18 (Dente et al., 1983. Nucl. Acids Res. 11, 645) was digested with HincII, treated with CIP and ligated to the 335 fragment to create pAbT764, as shown in FIG. 15C.

pAbT766 was digested with SphI, then partially digested with XhoI, and the resulting 1500 bp fragment containing the middle of the gII gene was gel-purified. pAbT764 was digested with SphI and XhoI, and the resulting 4270 bp fragment was gel-purified and then ligated to the 1500 bp fragment to create pAbT780, as shown in FIG. 15D.

pAbT6016 was partially digested with HindIII and then was completely digested with BamHI. The resulting 14,600 bp fragment was gel-purified, treated with mung bean nuclease and then re-ligated to create pAbT4030, as shown in FIG. 16A.

pAbT4030 was digested with BglII and the resulting 3900 bp fragment containing the BamF-lacZ gene was gel-purified. pAbT4027 was partially digested with BglII and treated with CIP, and the resulting 4800 bp fragment was gel-purified. The two fragments were ligated to create pAbT4032, as shown in FIG. 16B.

pAbT765 was digested with SphI, partially digested with SalI and the resulting 1700 bp fragment, containing the 3′ end of the gIII gene, was gel-purified. pAbT4032 was digested with SphI and SalI, treated with CIP and ligated to the 1700 bp fragment to create pAbT763, as shown in FIG. 16C.

pAbT763 was digested with XbaI and KpnI, and the resulting 2120 bp fragment was gel-purified. pAbT4027 was digested with XbaI and KpnI, then treated with CIP, and the resulting 8280 bp fragment was gel-purified. The two fragments were ligated to create pAbT769, as shown in FIG. 16D.

pAbT780 was digested with XbaI and SphI, and the resulting 1770 bp fragment, containing the 5′ end of the gII gene, was gel-purified. pAbT769 was digested with XbaI and SphI, then treated with CIP and ligated to the 1700 bp fragment to create pAbT781, as shown in FIG. 16E.

PAbT781 is a vector for the insertion and expression of the gene encoding pseudorabies gII in vaccinia virus. PAbt781contains the same elements for bacterial growth and selection and vaccinia recombination and selection as pAbT752 described in Example 1. PAbT781 differs from pAbT752 in that PAbT781 contains the PrV gII gene under the control of the vaccinia 7.5K promoter, and contains the vaccinia 30K promoter followed by a unique restriction site for insertion and expression of a second foreign antigen.

EXAMPLE 13

Recombinant Vaccinia Virus Containing the Gene Encoding PrV gp50 Under the Control of the Vaccinia 11KΔ5 Promoter by in Vivo Recombination (IVR)

In vivo recombination is a method whereby recombinant vaccinia viruses are created (Nakano et al., 1982. Proc. Natl. Acad. Sci. USA 79, 1593.) These recombinant viruses are formed by transfecting DNA containing a gene of interest into cells which have been infected by wild type vaccinia virus (in this case NYCBH). A small percent of the progeny virus will contain the gene of interest integrated into a specific site on the vaccinia genome. These recombinant viruses can express genes of foreign origin (Panicali and Paoletti., 1982. Proc. Natl. Acad. Sci. USA 79, 4927; Panicali et al., 1983. Proc. Natl. Acad. Sci. USA 80, 5364).

pAbT756 DNA was transfected into CV-1 cells which had been infected with the NYCBH strain of vaccinia virus at an MOI of 2. The selection system for recombinant virus was the appearance of blue plaques due to the metabolism of Bluo-Gal directed by the lacZ gene introduced on pAbT756 and integrated into the vaccinia genome. Approximately $1 \times 10^6$ CV-1 cells on a 6 cm plate were infected for 40 min at 37° C. After adsorption, 3.3 ml of MEM-2% FSC was added to the plate. For the calcium phosphate precipitation of DNA, 236.6 ul of Buffer A was added to 20 ug of pAbT756 DNA (originally at a concentration of 1.5 mg/ml), followed by the addition of 250 ul of Buffer B as described in Materials and Methods. After 40 min, this DNA was added dropwise to the infected cells, which were then incubated at 37° C. until 100% of the cells were observed to be infected.

The infected cells and virus were harvested and the undiluted and diluted ($10^{-1}$ to $10^{-3}$) virus was titrated as previously detailed. Virus was diluted 1:5 and 0.5 ml was adsorbed onto each of ten 6 cm plates of CV-1 cells; this infection yielded 1,000 plaques per plate. Several blue plaques were picked from these plates, and after five cycles of plaque purification, four final blue plaques were picked and amplified twice on 6 cm CV-1 plates. One of these was amplified on a 15 cm plate and concentrated by centrifugation through a 36% (w/v) sucrose cushion as already described. This virus, designated vAbT20, had a final concentration of $2.72 \times 10^{10}$ PFU/ml. Expression of the gp50 gene by this virus was analyzed as described in Example 19.

EXAMPLE 14

Recombinant Vaccinia Virus Containing the Gene Encoding PrV gIII, Under the Control of the Vaccinia 7.5K Promoter, by in vivo Recombination (IVR)

pAbT501 DNA was transfected into CV-1 cells which had been infected with the NYCBH strain of vaccinia virus at an MOI of 2. The selection system for recombinant virus was the appearance of blue plaques due to the metabolism of Bluo-Gal directed by the lacZ gene introduced on the pAbT501 plasmid and integrated into the vaccinia genome. Approximately $1 \times 10^6$ CV-1 cells on a 6 cm plate were infected for 40 min at 37° C. After adsorption, 3.3 ml of MEM-2% FCS was added to the plate. For the calcium phosphate precipitation of DNA, 240 ul of Buffer A was added to 20 ug of pAbT501 DNA (originally at a concentration of 2.0 mg/ml), followed by the addition of 250 ul of Buffer B as described in Material and Methods. After 40 min, this DNA was added dropwise to the infected cells, which were then incubated at 37° C. until 100% of the cells were observed to be infected.

The infected cells and virus were harvested and the virus was titrated as previously detailed. The $10^{-2}$ dilution resulted in 250-300 plaques per plate and fourteen 6 cm plates of CV-1 cells were each infected with 0.5 ml of the $10^{-2}$ dilution of virus obtained from the IVR. Ten blue plaques were picked from these plates, and after four cycles of plaque purification, twelve final blue plaques were picked. Of these, six were amplified twice on 6 cm CV-1 plates. Two of these, vAbT67-9-1-1-1 and vAbT67-9-1-2-1, were amplified on 15 cm plates and concentrated by centrifugation through a 36% (w/v) sucrose cushion as already described. One isolate, vAbT67-9-1-2-1, was picked for further amplification in a HeLa-S3 spinner culture. The virus was centrifuged through a 25-40% (w/v) sucrose gradient in an SW28 rotor at 15,000 rpm at 4° C. for 40 min. This preparation yielded virus at a final concentration of $2.93 \times 10^9$ PFU/ml. Expression of the PrV gIII gene by this recombinant was analyzed as described in Examples 19, 20 and 22.

EXAMPLE 15

Recombinant Vaccinia Virus Containing the Gene Encoding PrV gp50 Under the Control of the Vaccinia 7.5K Promoter by in vivo Recombination (IVR)

pAbT4018 DNA was transfected into CV-1 cells which had been infected with vaccinia virus cells at an MOI of 2. The virus strain was NYCBH and the selection system for recombinant virus was the appearance of blue plaques due to the metabolism of Bluo-Gal directed by the lacZ gene. Approximately $1 \times 10^6$ CV-1 cells on a 6 cm plate were infected for 40 min at 37° C. After adsorption, 3.3 ml of MEM-2% FCS was added to the plate. For the calcium phosphate precipitation of DNA, 210 ul of Buffer A was added to 20 ug of pAbT4018 DNA (originally at a concentration of 0.5 mg/ml), followed by the addition of 250 ul of Buffer B as already described. After 40 min, this DNA was added dropwise to the infected cells, which were then incubated at 37° C. until 100% of the cells were observed to be infected.

The infected cells and virus were harvested and the virus was titrated as previously detailed. The $5 \times 10^{-3}$ dilution resulted in 250-300 plaques per plate and twenty-two 6 cm plates of CV-1 cells were each infected with 0.5 ml of the $5\times10^{-3}$ dilution of virus obtained from the IVR. Three blue plaques were picked from these plates, and after four cycles of plaque purification, eight final blue plaques were picked and three (vAbT54R-1-1-1-1, vAbT54R-1-1-2-1 and vAbT54R-3-1-1-1-) were amplified twice on 6 cm CV-1 plates. All three were then amplified on 15 cm plates and concentrated by centrifugation through a 36% (w/v) sucrose cushion as already described. One isolate, vAbT54-1-1-1-1, was picked for further amplification in a HeLa-S3 spinner culture. The virus was centrifuged through a 25–40% (w/v) sucrose gradient in an SW28 rotor at 15,000 rpm at 4° C. for 40 min. This preparation yielded virus at a final concentration of $2.0\times10^{11}$ PFU/ml. Expression of gp50 antigen by this recombinant was analyzed as described in Examples 19, 20 and 21.

EXAMPLE 16

Recombinant Vaccinia Virus Containing the Gene Encoding PrV gIII, Under Control of the Vaccinia 11KΔ 5 promoter, by in vivo Recombination (IVR)

pAbT50 2 DNA was transfected into CV-1 cells which had been infected with vaccinia virus cells at an MOI of 2. The virus strain was NYCBH and the selection system for recombinant virus was the appearance of blue plaques due to the metabolism of Bluo-Gal directed by the lacZ gene. Approximately $1\times10^6$ CV-1 cells on a 6 cm plate were infected for 40 min at 37° C. After adsorption, 3.3 ml of MEM-2% FCS were added to the plate. For the calcium phosphate precipitation of DNA, 243.3 ul of Buffer A was added to 20 ug of pAbT502 DNA (originally at a concentration of 3.00 mg/ml), followed by the addition of 250 ul of Buffer B as already described. After 40 min, this DNA was added dropwise to the infected cells, which were then incubated at 37° C. until 100% of the cells were observed to be infected.

The infected cells and virus were harvested and the virus was titrated as previously detailed. The $10^{-2}$ dilution resulted in 250–300 plaques per plate and twenty-one 6 cm plates of CV-1 cells were each infected with 0.5 ml of the $10^{-2}$ dilution of virus obtained from the IVR. Six blue plaques were picked from these plates, and after four cycles of plaque purification, eight final blue plaques were picked and four of them were amplified twice on 6 cm CV-1 plates. Two of these virus isolates were further amplified on 15 cm plates and concentrated by centrifugation through a 36% (w/v) sucrose cushion as already described. One isolate, vAbT69-1-1-1-1, was picked for further amplification in a HeLa-S3 spinner culture. The virus was centrifuged through a 25–40% (w/v) sucrose gradient in an SW28 rotor at 15,000 rpm at 4° C. for 40 min. This preparation yielded virus at a final concentration of $2.88\times10^9$ PFU/ml. Expression of gIII antigen by this recombinant is described in Example 19.

EXAMPLE 17

Recombinant Vaccinia Virus Containing PrV gp50 Under the Control of the Vaccinia 7.5K Promoter and PrV gIII Under the Control of the Vaccinia 30K Promoter by in vivo Recombination (IVR)

pAbT503 DNA was transfected into CV-1 cells which had been infected with vaccinia virus cells at an MOI of 0.5. The virus strain was NYCBH and the selection system for recombinant virus was the appearance of blue plaques due to the metabolism of Bluo-Gal directed by the lacZ gene. Approximately $1\times10^6$ CV-1 cells on a 6 cm plate were infected for min at 37° C. with 50 ul of virus mixed with 150 ul of MEM-2% FCS. After adsorption, 3.3 ml of MEM-2% FCS was added to the plate. For the calcium phosphate precipitation of DNA, 230 ul of Buffer A was added to 20 ug of pAbT503 DNA (originally at a concentration of 1.0 mg/ml), followed by the addition of 250 ul of Buffer B as already described. After 40 min, this DNA was added dropwise to the infected cells, which were then incubated at 37° C. until 100% of the cells were observed to be infected.

The infected cells and virus were harvested and the virus was titrated as previously detailed. The $10^{-4}$ dilution resulted in 250–300 plaques per plate and five blue plaques were picked from these plates. After two cycles of plaque purification, five blue plaques (vAbT78A) were picked for analysis of gene expression by black plaque assay as described in Example 19.

EXAMPLE 18

Recombinant Vaccinia Virus Containing PrV gIII Under the Control of the 7.5K Promoter and gp50 Under the Control of the 30K Promoter by in vivo Recombination (IVR)

pAbT506 was transfected into CV-1 cells which had been infected with vaccinia virus at an MOI of 0.5. The virus strain was NYCBH and the selection system for recombinant virus was the appearance of blue plaques due to the metabolism of Bluo-Gal directed by the lacZ gene. Approximately $1\times10^6$ CV-1 cells on a 6 cm plate were infected for 40 min at 37° C. with 50 ul of virus diluted with 150 ul of MEM-2% FCS. After adsorption, 3.3 ml of MEM-2% FCS was added to the plate. For the calcium phosphate precipitation of DNA, 230 ul of Buffer A was added to 20 ug of pAbT506 DNA (originally at a concentration of 1.0 mg/ml), followed by the addition of 250 ul of Buffer B as already described. After 40 min, the DNA was added dropwise to the infected cells, which were then incubated at 37° C. until 100% of the cells were observed to be infected.

The infected cells and virus were harvested and the virus was titrated as previously detailed. The $10^{-4}$ dilution resulted in 250–300 plaques per plate. Five blue plaques were picked from these plates, and after two cycles of plaque purification, eight blue plaques (vAbT90) were picked for analysis of gene expression by black plaque assay as described in Example 19.

EXAMPLE 19

Black Plaque Assay for Expression of PrV Antigens gp50 and gIII in Vaccinia.

The black plaque assay, described in Materials and Methods, is an in situ enzyme-based immunoassay which can detect protein expressed by vaccinia-infected cells.

The black plaque assay was performed on the monovalent vaccinia recombinants vAbT20, vAbT54, vAbT67 and vAbT69; they contained, respectively, the gene encoding PrV gp50 under the control of the vaccinia 11KΔ5 promoter, the gene encoding gp50 under the control of the 7.5K promoter, the gene encoding gIII under the control of the 7.5K promoter and the gene encoding gIII under the control of the 11KΔ5 promoter. Monoclonal antibodies M4, M6, M7 (anti-gIII) and MCA50 (anti-gp50) were used.

Plaques formed by the negative control, NYCBH virus, showed only a background color which was consistent with the background on the cell monolayer itself. Plaques formed by the vaccinia recombinant, however, stained a distinct dark purple color which was much darker than the background on the cell monolayer. These results were obtained with all appropriate anti-PrV antibodies, and showed that all the recombinants were expressing the appropriate PrV gp50 or gIII antigen.

EXAMPLE 20

Enzyme-linked Immunosorbance Assay (ELISA) for PrV Antigen Expression

ELISAs were performed as described in Materials and Methods on lysates of CV-1 cells infected with vAbT54 (gp50 recombinant), vAbT67 (gIII recombinant) and NYCBH (wild-type strain). The results are summarized in Table 1. Monoclonal antibody MCA50 to gp50 recognized an antigen in cells infected with vAbT54 but not in cells infected with NYCBH virus. Monoclonal antibodies to gIII (M4, M6 and M7) recognized an antigen in cells infected with vAbT67 but not in cells infected with NYCBH virus.

TABLE 1

Results of ELISA on Cells Infected with Vaccinia Recombinants Expressing gp50 and gIII

| Monoclonal Antibody | Specificity | Cells Infected with: vAbT54 (gp50) | vAbT67 (gIII) | NYCBH |
|---|---|---|---|---|
| M4 | gIII | 0.15 | 1.29 | 0.17 |
| M6 | gIII | 0.15 | 1.31 | 0.15 |
| M7 | gIII | 0.19 | 0.99 | 0.17 |
| MCA50 | gp50 | 0.42 | 0.18 | 0.14 |

Results are expressed as average of duplicate 0.D. readings at 450 nm.

EXAMPLE 21

Immunoprecipitation of PrV gp50 From Recombinant Vaccinia

Immunoprecipitation analysis was performed on CV-1 cells infected with recombinant vaccinia virus, vAbT54, containing the gene encoding the glycoprotein gp50 of PrV under the control of vaccinia 7.5K Cells were labeled with either [$^{35}$S]methpromoter. ionine or [$^{3}$H]glucosamine for approximately 20 hours. The cell lysates were precleared three times using an anti-vaccinia virus serum and then incubated with swine anti-PrV serum at a dilution of 1:100. Antibodies were precipitated using *S. aureus*, and the crossreacting antigens were inspected by SDS-polyacrylamide gel electrophoresis followed by autoradiography.

Two (vAbT54R-1-1-1-1 and vAbT54R-1-1-2-1) vaccinia-gp50 recombinants incorporated [$^{35}$S] methionine predominantly into a 55,000 dalton protein which co-migrated with a PrV protein of the same size. This protein was also detected when the samples were radiolabeled with [$^{3}$H]glucosamine, thereby confirming its identity as a glycoprotein. The signal was absent in mock-infected CV-1 cells, in cells infected with wild-type vaccinia virus and in cells infected with recombinant virus containing the gene for the VP1 protein of canine parvovirus.

EXAMPLE 22

Immunoprecipitation of PrV gIII from Recombinant Vaccinia

Immunoprecipitation analysis of vaccinia recombinant virus vAbT67 containing the gIII glycoprotein of PrV was performed essentially as described in Example 21. A high level of gIII expression was obtained in two recombinants which carried the gIII gene under the control of the 7.5K promotor. When these samples were labeled with either [$^{35}$S]methionine or [$^{3}$H]glucosamine, the autoradiogram of the SDS gel showed a very strong signal corresponding to a glycoprotein of molecular weight 92,000 daltons, and a weaker signal for a glycoprotein of 74,000 daltons. These molecular weights agree with those reported for the fully and partially glycosylated forms of a protein determined to be gIII (Robbins et al., 1986. J. Virol. 58, 39).

EXAMPLE 23

Black Plaque Assay with Immune Serum of Mice Immunized with Recombinant Vaccinia Virus Expressing Pseudorabies gp50 on gIII Mice were injected with vaccinia recombinant vAbT54R, expressing pseudorabies gp50 under the control of the 7.5K promoter, or with vaccinia recombinant vAbT67, expressing pseudorabies gIII under the control of the 7.5K promoter, as described in Materials and Methods.

Sera were obtained two weeks after injection and tested against PrV by a black plaque assay as described in Materials and Methods. Serum from mice immunized with vAbT54R and vAbT67 both reacted strongly with the PrV plaques at all dilutions of serum. Serum from mice immunized with vAbT53 (an unrelated recombinant vaccinia virus.) did not react at all with the PrV plaques. Thus, recombinant viruses vAbT54R and vAbT67 elicit an immune response to PrV glycoproteins gp50 and gIII in mice.

EXAMPLE 24

Neutralization Assay with Immune Serum of Rabbits and Mice Immunized with Recombinant Vaccinia Virus vAbT54R Expressing Pseudorabies Glycoprotein gp50

One New Zealand white rabbit was immunized S.C. on the back with 108 PFU of vaccinia recombinant vAbT54R which expresses pseudorabies glycoprotein gp50 under the control of the 7.51 promoter. Serum obtained on day 21 after immunization was used in the neutralization assay. Balb/c mice were immunized I.P. with $10^7$ PFU of vAbT54R. Serum obtained on day 21 after immunization was used for the neutralization assay. Serum obtained from a rabbit and mouse immunized with vaccinia recombinant vAbT53, which expresses an antigen unrelated to PrV, was used as a negative control. The antisera from both mouse and rabbit vaccinated with vAbT54R inhibited plaque formation by PrV on BHK-21 cells, while the control vAbT53 antisera did not, demonstrating that antisera raised against a recombinant vaccinia virus expressing PrV glycoprotein gp50 neutralizes pseudorabies.

DEPOSIT OF PLASMIDS

The following plasmids have been deposited on Sep. 19, 1986 at the American Tissue Type Collection in Rockville, Md. and assigned the designated accession numbers:

| Plasmid | Accession Number |
| --- | --- |
| pAbT501 | 67211 |
| pAbT502 | 67212 |
| pAbT503 | 67213 |
| pAbT506 | 67214 |
| pAbT771 | 67215 |
| pAbT4018 | 67216 |

EQUILAVENTS

Those skilled in the art will recognize, or be able to ascertain using no more than routine experimentation, many equivalents to the specific embodiments of the invention described herein. Such equivalents are intended to be encompassed by the following claims.

We claim:

1. A recombinant vaccinia virus comprising, in a region of the viral genome nonessential for replication of the virus, a gene encoding a gp50 envelope glycoprotein of pseudorabies virus and a gene encoding a marker or indicator protein, each gene being under transcriptional control of a separate vaccinia viral promoter, said promoters oriented in the same transcriptional direction, wherein the recombinant vaccinia virus is capable of eliciting a protecting immune response to the encoded gp50 glycoprotein in a host animal, wherein said recombinant vaccinia virus is vAbT54R or vAbT90.

2. The recombinant vaccinia virus of claim 1 which is vAbT54R.

3. The recombinant vaccinia virus of claim 1 which is vAbT90.

* * * * *